US012565673B2

(12) United States Patent
Chakrabarti et al.

(10) Patent No.: US 12,565,673 B2
(45) Date of Patent: Mar. 3, 2026

(54) METHODS FOR THE DESIGN OF NONALLOSTERIC SIRTUIN ACTIVATING COMPOUNDS

(71) Applicant: Chakrabarti Advanced Technology, LLC, Mt. Laurel, NJ (US)

(72) Inventors: Raj Chakrabarti, Moorestown, NJ (US); Xiangying Guan, Cherry Hill, NJ (US); Alok Upadhyay, Mount Laurel, NJ (US)

(73) Assignee: CHAKRABARTI ADVANCED TECHNOLOGY LLC, Mt. Laurel, NJ (US)

(*) Notice: Subject to any disclaimer, the term of this patent is extended or adjusted under 35 U.S.C. 154(b) by 1226 days.

(21) Appl. No.: 17/356,237

(22) Filed: Jun. 23, 2021

(65) Prior Publication Data

US 2022/0002778 A1    Jan. 6, 2022

Related U.S. Application Data

(60) Provisional application No. 63/042,925, filed on Jun. 23, 2020.

(51) Int. Cl.
| | |
|---|---|
| *C12Q 1/34* | (2006.01) |
| *C12N 9/80* | (2006.01) |
| *G01N 33/573* | (2006.01) |
| *G16B 15/20* | (2019.01) |

(52) U.S. Cl.
CPC ................ *C12Q 1/34* (2013.01); *C12N 9/80* (2013.01); *G01N 33/5735* (2013.01); *C12Y 305/01098* (2013.01); *G01N 2333/98* (2013.01); *G01N 2500/04* (2013.01); *G16B 15/20* (2019.02)

(58) Field of Classification Search
CPC ........ C12Q 1/34; C12N 9/80; G01N 33/5735; G01N 2333/98; G01N 2500/04; G01N 2500/00; C12Y 305/01098; G16B 15/20; G16B 35/10; G16B 35/20
See application file for complete search history.

(56) References Cited

U.S. PATENT DOCUMENTS

| | | | | |
|---|---|---|---|---|
| 11,118,211 | B2 * | 9/2021 | Chakrabarti | ....... G01N 33/5014 |
| 2018/0258464 | A1 * | 9/2018 | Chakrabarti | ............. C12Q 1/48 |

OTHER PUBLICATIONS

Upadhyay, A et al. "Nonallosteric Sirtuin Enzyme Activation: Characterization of Hit Compounds". bioRxiv preprint. https://doi.org/10.1101/2020.04.17.045187. May 22, 2020. (Year: 2020).*

Guan, X. et al. Mechanism of Inhibition of the Human Sirtuin Enzyme SIRT3 by Nicotinamide: Computational and Experimental Studies. PLOS One, 2014, 9, 9, e107729. (Year: 2014).*

(Continued)

*Primary Examiner* — Karlheinz R. Skowronek
*Assistant Examiner* — Diana P Sanford
(74) *Attorney, Agent, or Firm* — J. Clinton Wimbish; Maynard Nexsen PC

(57) ABSTRACT

The present invention provides workflows for the discovery of nonallosteric sirtuin activation compounds. Workflows enable drug discovery of novel sirtuin activating compounds with prescribed effects on the binding in pockets near the active site interacting with flexible protein degrees of freedom around the active site. Novel kinetic models are used to confirm hit compounds and to improve their properties.

18 Claims, 30 Drawing Sheets

Specification includes a Sequence Listing.

(56)                    References Cited

OTHER PUBLICATIONS

Zhang X, Perez-Sanchez H, Lightstone Fc. A Comprehensive Docking and MM/GBSA Rescoring Study of Ligand Recognition upon Binding Antithrombin. Curr Top Med Chem. 2017;17(14):1631-1639. doi: 10.2174/1568026616666161117112604. (Year: 2017).*

Jin, L et al. Crystal structures of human SIRT3 displaying substrate-induced conformational changes. J Biol Chem. Sep. 4, 2009;284(36):24394-405. doi: 10.1074/jbc.M109.014928. Epub Jun. 16, 2009. PMID: 19535340; PMCID: PMC2782032. (Year: 2009).*

Lu J. et al. A small molecule activator of SIRT3 promotes deacetylation and activation of manganese superoxide dismutase. Free Radic Biol Med. Nov. 2017;112:287-297. doi: 10.1016/j.freeradbiomed.2017.07.012. Epub Jul. 12, 2017. PMID: 28711502. (Year: 2017).*

Guan X, Upadhyay A, Munshi S, Chakrabarti R (2018) Biophysical characterization of hit compounds for mechanism-based enzyme activation. PLoS One 13(3): e0194175. https://doi. org/10.1371/journal.pone.0194175 (Year: 2018).*

\* cited by examiner

Sirt3/NAD+/Ac-ACS/48VG loop (a)

$$K_{m,NAD^+,app} \approx \frac{c_{11}\left(1+\frac{[A]}{K_{d1,A}}\right)}{c_{21}\left(1+\frac{[A]}{K_{d2,A}}\right)+c_{31}\left(1+\frac{[A]}{K_{d3,A}}\right)+c_{41}\left(1+\frac{[A]}{K_{d4,A}}\right)+c_{51}\left(1+\frac{[A]}{K_{d5,A}}\right)}$$

$$\approx k_{cat,app}\left(\frac{1}{k_1}+\frac{K_{d,NAD+}}{k_2}\right)\frac{1+[A]/K_{d1,A}}{1+[A]/K_{d4,A}} \approx k_{cat,app}\left[\frac{1}{k_1}+\frac{K_{d,NAD+,app}}{k_2}\frac{\frac{1+[A]/K_{d2,A}}{1+[A]/K_{d1,A}}}{1+c_{51}\left(1+\frac{[A]}{K_{d5,A}}\right)\frac{1+[A]/K_{d1,A}}{1+[A]/K_{d4,A}}}\right]$$

(b)

$$\frac{1}{K_{3,app}} \approx \frac{c_{22}\left(1+[A]/K_{d2,A}\right)+c_{32}\left(1+[A]/K_{d3,A}\right)+c_{53}\left(1+[A]/K_{d5,A}\right)}{c_{21}\left(1+[A]/K_{d2,A}\right)+c_{31}\left(1+[A]/K_{d3,A}\right)+c_{41}\left(1+[A]/K_{d4,A}\right)+c_{51}\left(1+/K_{d5,A}\right)} \approx \frac{1+K_{ex}}{K_{d,NAM}}\frac{\left(1+[A]/K_{d2,A}\right)}{\left(1+[A]/K_{d4,A}\right)}$$

(c)

$$\frac{1}{K_{2,app}} \approx \frac{c_{12}\left(1+[A]/K_{d1,A}\right)+c_{52}\left(1+[A]/K_{d5,A}\right)}{c_{11}\left(1+[A]/K_{d1,A}\right)} \approx \frac{c_{12}\left(1+[A]/K_{d1,A}\right)}{c_{11}\left(1+[A]/K_{d1,A}\right)} = \frac{K_{d,NAD^+}K_{ex}}{K_{m,NAD^-}K_{d,NAM}}$$

(d)

$$\frac{1}{K_{1,app}} \approx \frac{1}{K_{d,NAM}}\frac{\left(1+[A]/K_{d3,A}\right)}{\left(1+[A]/K_{d4,A}\right)}$$

(e)

$$\alpha_{app}K_{m,NAD+,app} \approx K_{d,NAD+}\frac{K_{ex}}{1+K_{ex}}\frac{\left(1+[A]/K_{d1,A}\right)}{\left(1+[A]/K_{d2,A}\right)}$$

Fig. 16

SEQUENCE LISTING

```
<160> NUMBER OF SEQ ID NOS: 2

<210> SEQ ID NO 1
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: ACETYLATION

<400> SEQUENCE: 1

Lys Gly Glu Leu Leu Glu Ala Ile Lys Arg Asp Phe Gly Ser Phe Asp
1               5                   10                  15

Lys Phe
```

-continued

```
<210> SEQ ID NO 2
<211> LENGTH: 7
<212> TYPE: PRT
<213> ORGANISM: Artificial Sequence
<220> FEATURE:
<223> OTHER INFORMATION: Sythetic peptide
<220> FEATURE:
<221> NAME/KEY: MOD_RES
<222> LOCATION: (4)..(4)
<223> OTHER INFORMATION: ACETYLATION

<400> SEQUENCE: 2

Gln Pro Lys Lys Ala Met Cys
1               5
```

METHODS FOR THE DESIGN OF NONALLOSTERIC SIRTUIN ACTIVATING COMPOUNDS

RELATED APPLICATION DATA

The present application claims priority pursuant to 35 U.S.C. § 119(e) to U.S. Provisional Application Ser. No. 63/042,925 filed Jun. 23, 2020 which is incorporated herein by reference in its entirety.

SEQUENCE LISTING

An electronic sequence listing (060015-00018.txt; size 87.5 KB; date of creation Aug. 29, 2025) submitted herewith is incorporated by reference in its entirety.

BACKGROUND

Sirtuin (silent information regulator) enzymes, which catalyze $NAD^+$-dependent protein post-translational modifications, have emerged as critical regulators of many cellular pathways. In particular, these enzymes protect against age-related diseases and serve as key mediators of longevity in evolutionarily distant organismic models. Sirtuins are $NAD^+$-dependent lysine deacylases, requiring the cofactor $NAD^+$ to cleave acyl groups from lysine side chains of their substrate proteins.

A thorough understanding of sirtuin chemistry is not only of fundamental importance, but also of considerable medicinal importance, since there is enormous current interest to develop new mechanism-based sirtuin modulators. Its overall catalytic process has been suggested to proceed in two consecutive stages. The initial stage involves the cleavage of the nicotinamide moiety of NAD+ and the nucleophilic attack of the acetyl-Lys side chain of the protein substrate to form a positively charged O-alkylimidate intermediate. Nicotinamide-induced reversal of the intermediate (the so-called base exchange reaction) causes reformation of $NAD^+$ and acetyl-Lys protein. The energetics of this reversible reaction affects both the potency of nicotinamide (NAM) inhibition of sirtuins and the Michaelis constant for NAD+ ($K_{m,NAD+}$). The second stage of sirtuin catalysis, which includes the rate determining step, involves four successive steps that culminate in deacetylation of the Lys side chain of the protein substrate and the formation of O-acetyl ADP ribose coproduct.

Recently, in order to combat old age, intense interest has developed in the activation of the seven mammalian sirtuin enzymes (SIRT1-7). Compared to enzyme inhibitors, which constitute the vast majority of today's drugs, enzyme activators have considerable advantages. However, they are much more difficult to design, because enzymatic catalysis has been optimized over billions of years of evolution. Prior work on sirtuin activation has focused exclusively on experimental screening, with an emphasis on allosteric activation of the SIRT1 enzyme. Indeed, small molecule allosteric activators of SIRT1 have been demonstrated to induce lifespan extension in model organisms such as mice. Allosteric activation is one of four known modes by which small molecules can activate enzymes. They function by decreasing the dissociation constant for the substrate (the acetylated protein dissociation constant $K_{d,Ac\_Pr}$ for sirtuins).

Almost all known sirtuin activators allosterically target SIRT1 and do not bind in the active site. However, allosteric activators only work with certain substrates of SIRT1. It is now known that other sirtuins, including SIRT2, SIRT3 and SIRT6, play significant roles in regulating mammalian longevity. General strategies for the activation of any mammalian sirtuin (including activation of SIRT1 for other substrates) are hence of central importance, but not understood. In general, allosteric activation to decrease substrate $K_d$ will not be an option for enzyme activation, rending mechanism-based activation important.

Foundations for the rational design of mechanism-based activators have been lacking. Several types of mechanism-based sirtuin inhibitors have been reported recently in the literature, including Ex-527. However, mechanism-based activation has proven far more elusive, due to the difficulty in screening for the balance of properties needed for a modulator to bind the active site and accelerate catalysis. While there are many ways to inhibit an enzyme's mechanism, there are far fewer ways to activate it. Only a dozen or so distinct classes of small molecule enzyme activators are currently known, with only four known modes of activation across all families of enzymes. None of those modes of activation exploit the unique catalytic reaction mechanisms of the target enzymes.

Accordingly, there is a need for a mechanism-based method to design sirtuin activating compounds.

SUMMARY

The present invention provides workflows for the discovery of nonallosteric sirtuin enzymes activator distinct from any previously reported enzyme activator drug discovery strategies. The workflows include high-throughput screening of drug-like test compound libraries against one or more catalytically active sirtuin receptor complexes, identification of potential nonallosteric sirtuin activator hit compounds based on the predicted binding properties, and confirmation of hit compounds based on experimental kinetic and/or binding measurements. The hit compounds bind in pockets near the active site interacting with flexible protein degrees of freedom around the active site. The hit compounds have several unique properties—some display non-steady state activation accompanied by steady-state inhibition, or a greater level of non-steady state activation compared to steady-state activation, owing to the features of nonallosteric enzyme activation. Novel kinetic models are used to confirm hit compounds and to improve their properties.

In some embodiments, a method for identifying a test compound for a non-allosteric sirtuin activating compound (MB-STAC) comprises establishing a library of compounds on the basis of the compounds exhibiting computational docking with at least one sirtuin complex selected from the group consisting of sirtuin+peptide substrate complex, sirtuin+peptide substrate+$NAD^+$ complex, sirtuin+alkylimidate intermediate+NAM complex, sirtuin+alkylimidate complex, and sirtuin+O-AADPR complex. For example, in some embodiments, compounds of the library exhibiting computational docking with the sirtuin+peptide substrate+$NAD^+$ complex are identified as test compounds. Moreover, compounds of the library exhibiting computational docking with the sirtuin+peptide substrate+$NAD^+$ complex and engaging in binding interactions with the sirtuin cofactor binding loop can be identified as test compounds. In further embodiments, a compound of the library is identified as test compound if the compound:

a) exhibits computational docking with at least one of the sirtuin+peptide substrate+$NAD^+$ complex and sirtuin+alkylimidate intermediate+NAM complex; and b) ratios of dissociation constants for binding of the compound to the sirtuin+peptide substrate complex, sirtuin+peptide substrate+NAD$^+$ complex, sirtuin+al-kylimidate intermediate+NAM complex, and sirtuin+alkylimidate complex, denoted by $K_{d1,A}$; $K_{d2,A}$; $K_{d3,A}$; and $K_{d4,A}$ respectively, satisfy at least one of the following relations:

$$\frac{K_{d1,A}}{K_{d2,A}} \leq 1 \Leftrightarrow \frac{K'_{d,NAD+}}{K_{d,NAD+}} \geq 1$$

$$\frac{K_{d2,A}}{K_{d3,A}} \gg 1 \Leftrightarrow \frac{K'_{ex}}{K_{ex}} \ll 1$$

$$\frac{K_{d3,A}}{K_{d4,A}} \geq 1 \Leftrightarrow \frac{K'_{d,NAM}}{K_{d,NAM}} \geq 1$$

wherein ⇔ means equivalent to, wherein $K_{d,NAD+}$ is the dissociation constant for NAD$^+$, $K_{d,NAM}$ is the dissociation constant for NAM, and $K_{ex}$ is the exchange equilibrium constant, and wherein the ' sign denotes corresponding values in presence of the test compound.

Additionally, in some embodiments, a compound of the library is identified as test compound if dissociation constants for binding of the selected compound to the sirtuin+peptide substrate complex, sirtuin+peptide substrate+NAD$^+$ complex, sirtuin+alkylimidate intermediate complex, and sirtuin+O-AADPR complex, denoted by $K_{d1,A}$; $K_{d2,A}$; $K_{d4,A}$; and $K_{d5,A}$ respectively, satisfy the following relations:

$K_{d2,A}$ or $K_{d4,A}$ are less than predetermined threshold values; and $K_{d1,A}$ or $K_{d5,A}$ are greater than a predetermined threshold values.

In some embodiments, $K_{d1,A}$, $K_{d2,A}$, $K_{d4,A}$, and $K_{d5,A}$ are experimentally measured. Alternatively, these rate constant can be estimated by computational docking.

Once identified, the test compound is incubated with sirtuin enzyme (E), NAD$^+$, NAM, and a concentration of an acylated substrate peptide in an assay for deacylation activity. In some embodiments, the concentration of the acylated substrate peptide is a saturating concentration. The non-steady state ($v_{non-ss}$) rate of sirtuin enzyme-catalyzed deacylation is measured, and the test compound is identified as a hit compound when the test compound induces sirtuin enzyme activation at an [E]$_0$/[NAD$^+$]$_0$ ratio exceeding 0.01, and preferably at a value of this ratio that enables accurate measurement of activity at times when the enzyme concentration exceeds the product concentration In some embodiments, the [E]$_0$/[NAD$^+$]$_0$ ratio has a value greater than 0.25 and less than 1. Moreover, the ratio of initial enzyme concentration [E]$_0$ to initial test compound concentration is at least 0.088, in some embodiments.

In some embodiments, methods described herein further comprise assaying effects of the test compound on sirtuin non-steady state, steady-state and equilibrium parameters, the method comprising:

d) fitting following nonlinear model to steady state rate data:

$$\frac{v}{v_{max}} = \frac{[NAD^+]\left(1 + \frac{[NAM]}{K_1}\right)}{K_{m,NAD+}\left(1 + \frac{[NAM]}{K_2}\right) + [NAD^+]\left(1 + \frac{[NAM]}{K_3}\right)}$$

wherein v denotes initial deacylation rate, e) obtaining estimates of steady state parameters $v_{max}$, $K_{m,NAD+}$, $K_1$, $K_2$, $K_3$ in the absence of the test compound and $v_{max,app}$, $K_{m,NAD+,app}$, $K_{1,app}$, $K_{2,app}$, $K_{3,app}$ in the presence of the test compound at a nonzero concentration, wherein $$\alpha = \frac{K_3}{K_2} \approx \frac{K_{d,NAD+}}{K_{m,NAD+}};$$

$K_{d,NAD+} \approx \alpha^* K_{m,NAD+}$, and wherein the test compound is a hit compound if $K_{d, NAD+}$ in the presence of the test compound is less than $K_{d,NAD+}$ in the absence of the test compound.

In some embodiments, the test compound is a hit compound when the test compound further induced sirtuin inhibition in the steady state. Alternatively, a ratio of non-steady state sirtuin enzyme-catalyzed deacylation to steady state sirtuin enzyme-catalyzed deacylation is greater than 1.

These and other embodiments are further described in the following detailed description.

BRIEF DESCRIPTION OF THE DRAWINGS

FIG. 6(A) The superposition of the un-saturating NAD$^+$ and saturating MnSOD K122 peptide in the three formats of 10 mins, 100 µM NAD$^+$ (N=2); 10 mins, 100 µM NAD$^+$/100 µM NAM (N=2), and 30 min, 50 µM NAD$^+$ (N=3). FIG. 6(B) Activation of Sirt3 on MnSOD substrate in the presence of 10 uM HKL at $[E]_0/[NAD^+]=0.0176$ ($[E]_0=0.8807$ uM, $[NAD^+]=50$ uM, $[MnSOD]=600$ uM, 1.5 min, N=6). FIG. 6(C) Top: Activation of SIRT3 activity on p53-AMC substrate in the presence of 10 uM HKL at $[E]_0=0.349$ uM, $[NAD^+]=20$ uM, [FdL]=10 uM, 5 min (N=2). Bottom: Dose-response curve was measured under conditions where $[SIRT3]_0/[NAD^+]_0=0.3$, in the presence of 50 mM $NAD^+$ and 10 mM FdL2 peptide. FIG. 6(D) Structure of HKL, 5, 3'-Diallyl-2, 4'-dihydroxybiphenyl.

FIG. 7(B) 200 µM HKL. Enlargements of the intersection points are provided as insets (a) and (c). The time series plots of µM product formed vs. time (for selected small time points; see FIG. 13 for full time course) are provided as insets (b) and (d). The lines are the results of global fitting; the lines were not fit independently to the data points in the individual panels. The error bars that are not visible are too small to view at this scale.

FIG. 8(A) Double reciprocal plots for deacetylation initial rate measurements in the presence and absence of HKL at [NAM]=0 µM. The enlargement of intersection point is provided as inset. FIG. 8(B) Comparison of Dixon plots at $[NAD^+]=15000$ µM in the presence and absence of HKL. FIG. 8(C) Double reciprocal plots for deacetylation initial rate measurements in the presence and absence of HKL at [NAM]=5 mM. The enlargement of intersection point is provided as inset. FIG. 8(D) Comparison of Dixon plots at $[NAD^+]=3000$ µM in the presence and absence of HKL.

FIGS. 9(A and C) Pathways in the sirtuin reaction network. FIG. 9(B) Carba-NAD binding in the ternary complex: effect of mechanism-based modulator HKL. Binding of carba NAD (c-NAD) to Sirt3.Ac-MnSOD complex, in presence and absence of 6.25 µM HKL measured using MST. FIG. 9(D) HKL binding: effect of NAM. Binding of HKL to the Sirt3.Ac-MnSOD complex, in presence and absence of NAM, measured using MST.

FIG. 10(B) Honokiol binding in the coproduct complex: effect of NAM; FIG. 10(C) Honokiol binding in the product complex: effect of $NAD^+$.

FIG. 11(A) Pathways in the sirtuin reaction network—E, enzyme; Ac-Pr, acetylated peptide substrate; NAD, NAM adenine dinucleotide; A, modulator (HKL). FIG. 11(B) Binding of carba NAD (c-NAD) to Sirt3.Ac-p53-AMC complex, in presence and absence of 6.25 µM HKL measured using MST.

FIG. 11(C) Plot of product formation vs. time ($[NAD^+]=50$ uM, [MnSOD peptide]=10 uM, $[E]_0/[NAD^+]_0=0.3$). FIG. 11(D) Plot of product formation vs. time ($[NAD^+]=50$ uM, [FdL2 peptide]=10 uM, $[E]_0/[NAD^+]_0=0.3$).

FIG. 12(A) Single exponential fitting of DeAc-MnSOD formed vs. time (0-40 min) in the presence and absence of saturating (200 µM) [HKL] for 100 µM $NAD^+$, 100 µM NAM; FIG. 12(B) Corresponding linear rate fitting plots (initial rates). Sirt3 Activation by HKL. FIG. 12(C) Plot of product formation vs. time in the presence and absence of 10 uM HKL for $[NAD^+]=50$ uM, [MnSOD K122]=600 uM, $[E]_0/[NAD^+]_0=0.3$ (n=2). FIG. 12(D) Bar diagram of % relative activity vs. time (n=2) under the latter conditions. The horizontal dotted line depicts the initial enzyme concentration.

FIG. 16 provides the expressions (a)-(e) for each of the modulated steady state constants in the presence of a specified concentration [A] of the hit compound, according to one proposed mechanism-based enzyme activation theory.

FIG. 18(A) Double reciprocal plots for deacylation initial rate measurements in the presence of activator. Data used to construct the Dixon plot at saturating [NAD+] depicted in FIG. 18(B) are highlighted by the blue box on the y axis. (B) Dixon plots for initial rates of deacylation in the presence of activator. Predicted plateaus in these curves are indicated by the arrows. FIG. 18(C) Comparison of double reciprocal plots at [NAM]=0 µM with and without activator. FIG. 18(D) Dixon plots at 1/[NAD+]=0 compared with and without activator. "A" indicates a mechanism-based sirtuin activating compound.

FIG. 19(A) Saturating FdL peptide (250 µM) and un-saturating NAD+(25 µM) (N=2); FIG. 19(B) high NAD+(3000 µM) and un-saturating FdL peptide (30 µM) (N=2) in the presence of different concentrations of HKL range from 0-350 µM using label-free HPLC (red) and labeled FdL assay (blue). FIG. 19(C) 2.5 mM NAD+ and 6.25 μM un-saturating MnSODK122 peptide (N=5).

DETAILED DESCRIPTION

Embodiments described herein can be understood more readily by reference to the following detailed description, examples, and drawings. Elements, apparatus, and methods described herein, however, are not limited to the specific embodiments presented in the detailed description, examples and drawings. It should be recognized that these embodiments are merely illustrative of the principles of the present invention. Numerous modifications and adaptations will be readily apparent to those of skill in the art without departing from the spirit and scope of the invention.

In one aspect, principles of nonallosteric enzyme activation are applied herein to experimentally and computationally characterize small molecules that have been reported to be activators of the SIRT3 enzyme in order to determine whether these compounds possess the proposed characteristics of nonallosteric or mechanism-based sirtuin activating compounds (MB-STACs). We also extend this framework to include the modulation of active site structure by mechanism-based activators, as well as activation under physiologically relevant non-steady state conditions. This constitutes the first application of the theory for nonallosteric activation to experimental and computational data, and as such provides a foundation for drug development of MB-STACs. The approach described herein was employed to characterize the effects of the compound honokiol, which was reported to be a SIRT3 activator, on the human SIRT3 enzyme under equilibrium, steady state and non-steady state kinetic conditions. The mechanism whereby honokiol activates SIRT3 under physiologically relevant conditions was elucidated and can establish the principles whereby hit compounds like honokiol can be evolved into more potent SIRT3 activator lead compounds.

I. Computational Identification and Characterization of Hit Compounds for Nonallosteric Sirtuin Activation Nonallosteric, mechanism-based activators can modulate the distributions of local degrees of freedom whose conformations change during the reaction, which results in tradeoffs in the AAG's for various reactions steps upon stabilization of one such conformation. This is a critical distinction from allosteric activation, where the conformational changes stabilized by the modulator are not specifically associated with certain steps in the enzymatic reaction.

Figure 1:
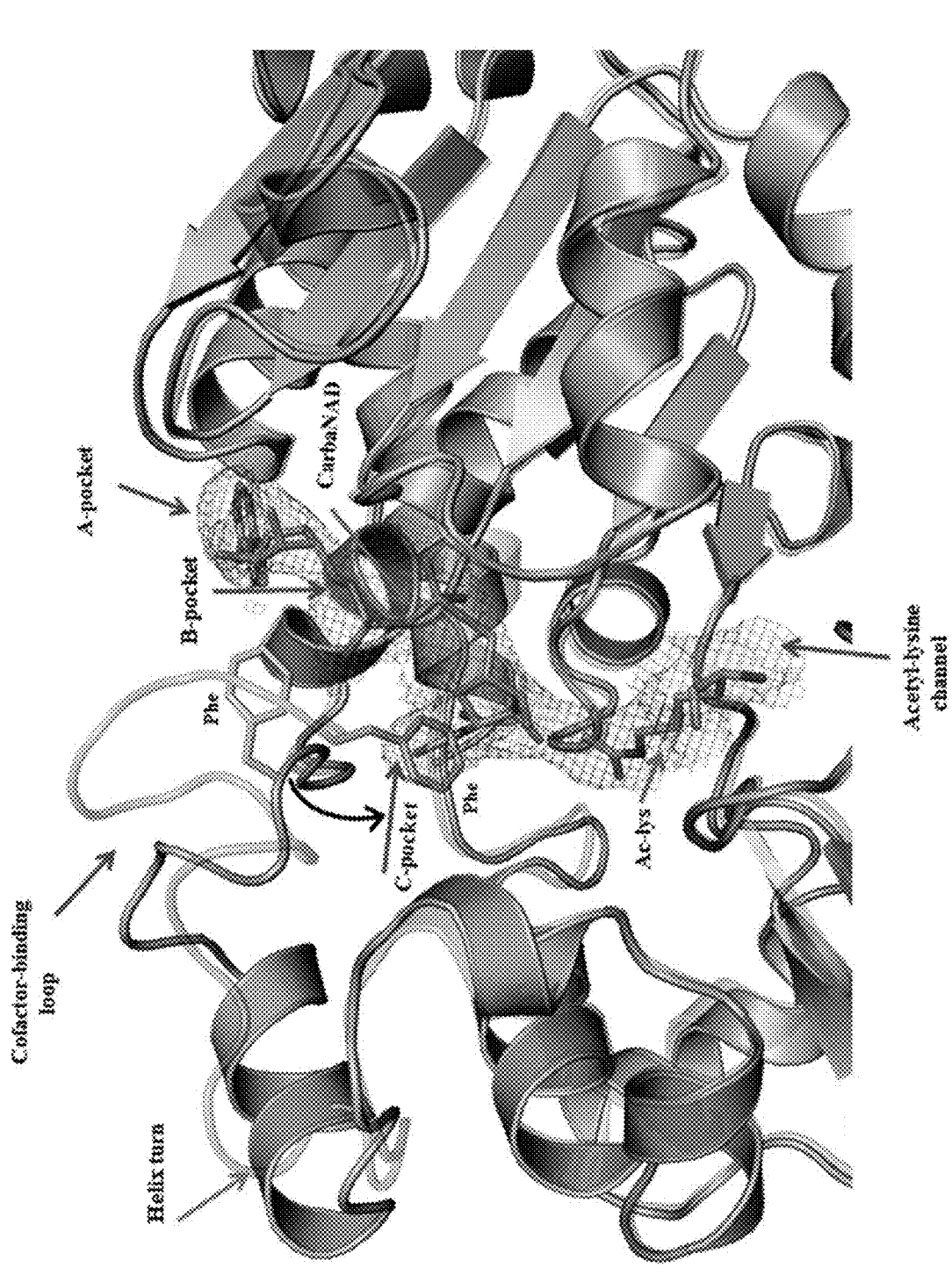
FIG. 1.—Superposition of Sirt3 native intermediate (4BVG) and Sirt3 ternary complex (4FVT) showing differences in the conformation of the cofactor binding loop and the position of the Phe 157 residue. Individual subsites are highlighted and the movement of Phe 157 is indicated by black arrows. The substrates Carba-NAD and Ac-Lysine are rendered in stick representation.

Activators of sirtuin enzymes that do not possess a known allosteric site have been shown through crystallographic studies to induce conformational changes in the so-called flexible cofactor binding loop in these enzymes. The conformation of this loop changes after the first chemical step of the reaction (cleavage of nicotinamide from the NAD$^+$ cofactor). For these activators, the local degrees of freedom above are the backbone degrees of freedom in the flexible cofactor binding loop. FIG. 1 presents a structural alignment that depicts this loop conformational change that occurs during the catalytic cycle of sirtuins.

Figure 2A:
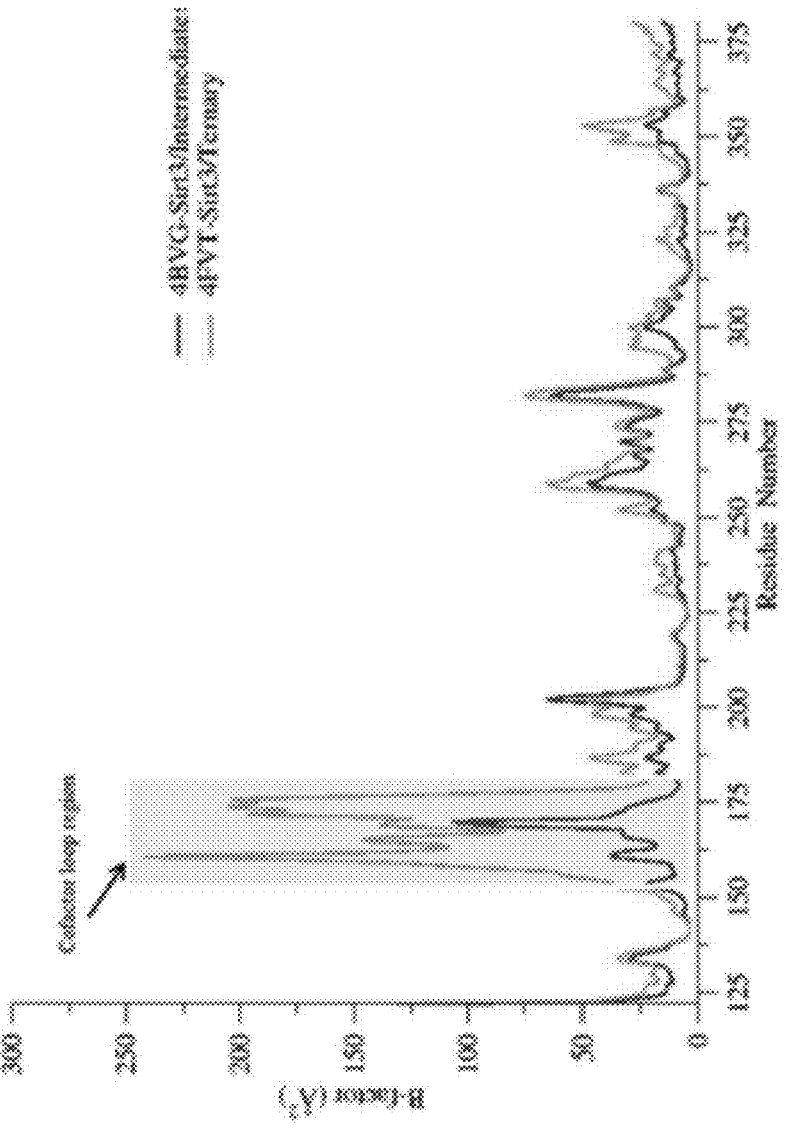
FIGS. 2(A)-2(B)—Plot showing simulated B-factor values for C$_\alpha$ atoms belonging to (A) residues 125-375; (B) the co-factor binding loop region of various SIRT3 complexes. Residues (162-170) are known to adopt a helix conformation when bound to substrate. Ternary=Ac-CS2/NAD$^+$ complex, Int=Intermediate FIG. 3(A)—Binding mode of Honokiol to the SIRT3 ternary complex (SIRT3: Ac-ACS2: NAD$^+$) by docking. Honokiol forms H-bonds with Glu 177 in the co-factor binding loop of SIRT3.
Figure 2B:
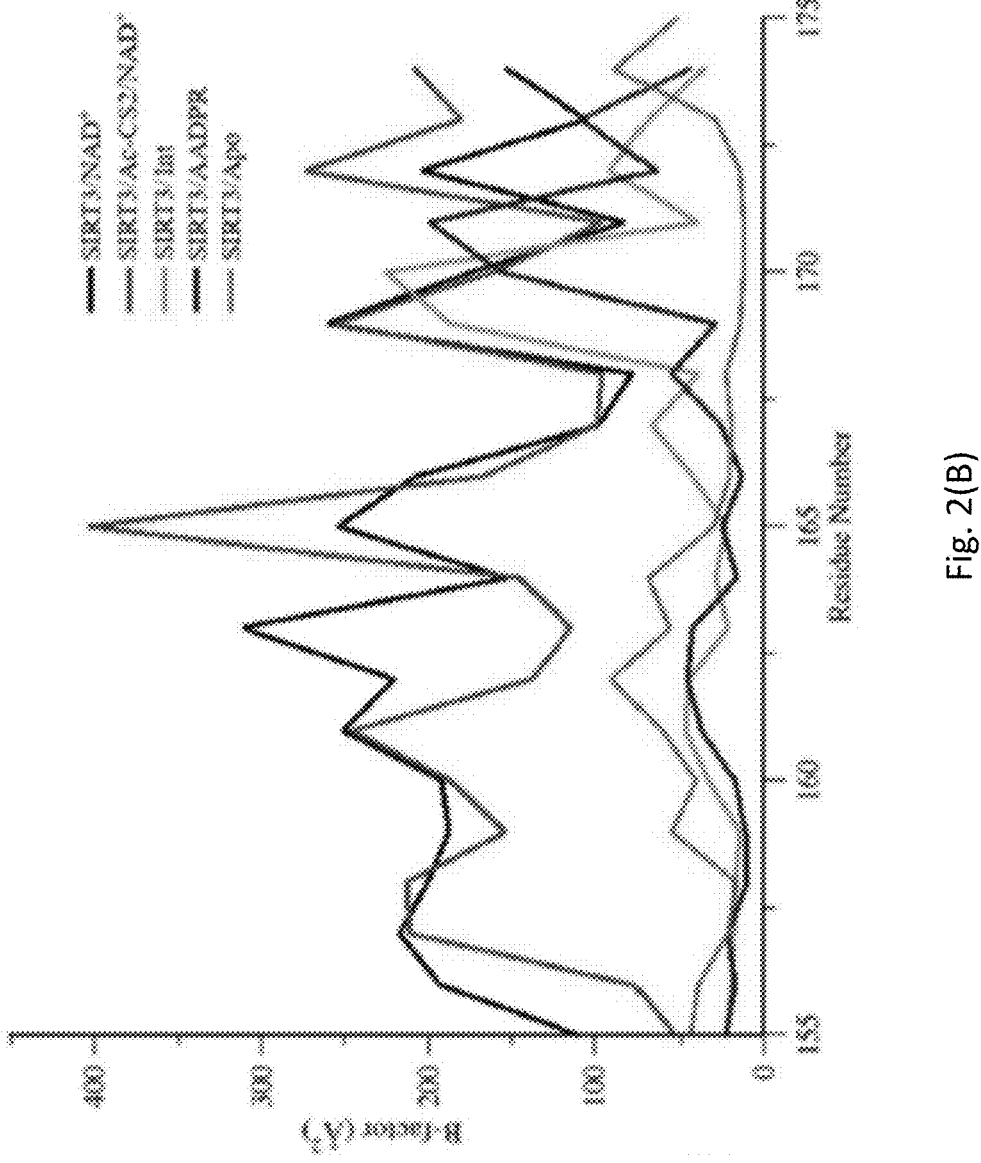

SIRT3, the major mitochondrial sirtuin, is one of the most important sirtuins implicated in regulating healthspan; hence, it was chosen as a subject of study. Molecular dynamics simulations were employed to study the flexibility of the SIRT3 cofactor binding loop in different conformations associated with the stages of the sirtuin catalytic cycle (FIG. 2). The high B factors for the ternary complex cofactor binding loop are consistent with the ability of modulator binding near the loop to alter its conformation.

Figure 3A:
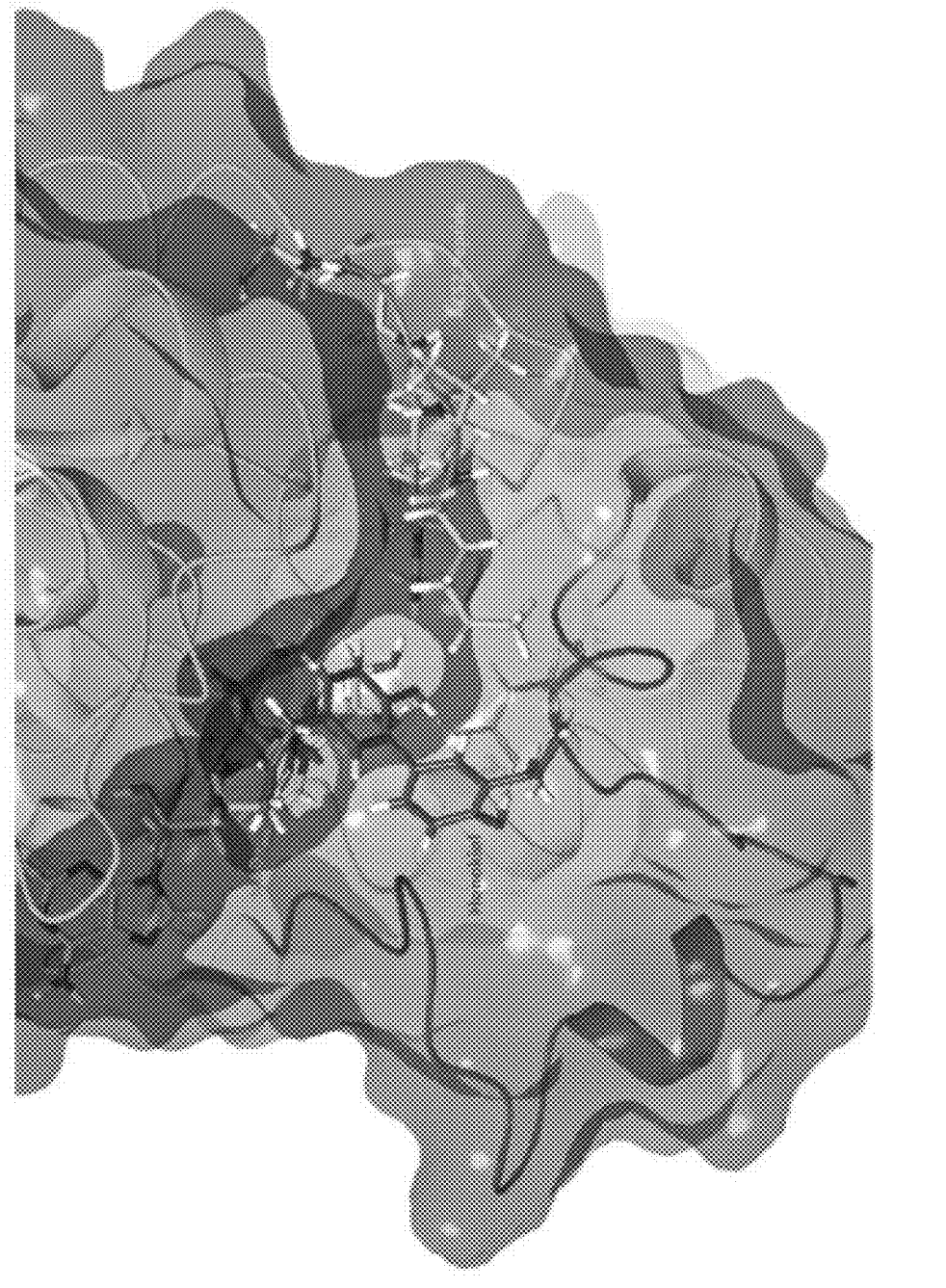
FIG. 3(B)—Close-up view of FIG. 3(A) highlighting Honokiol interactions with the loop.
Figure 3B:
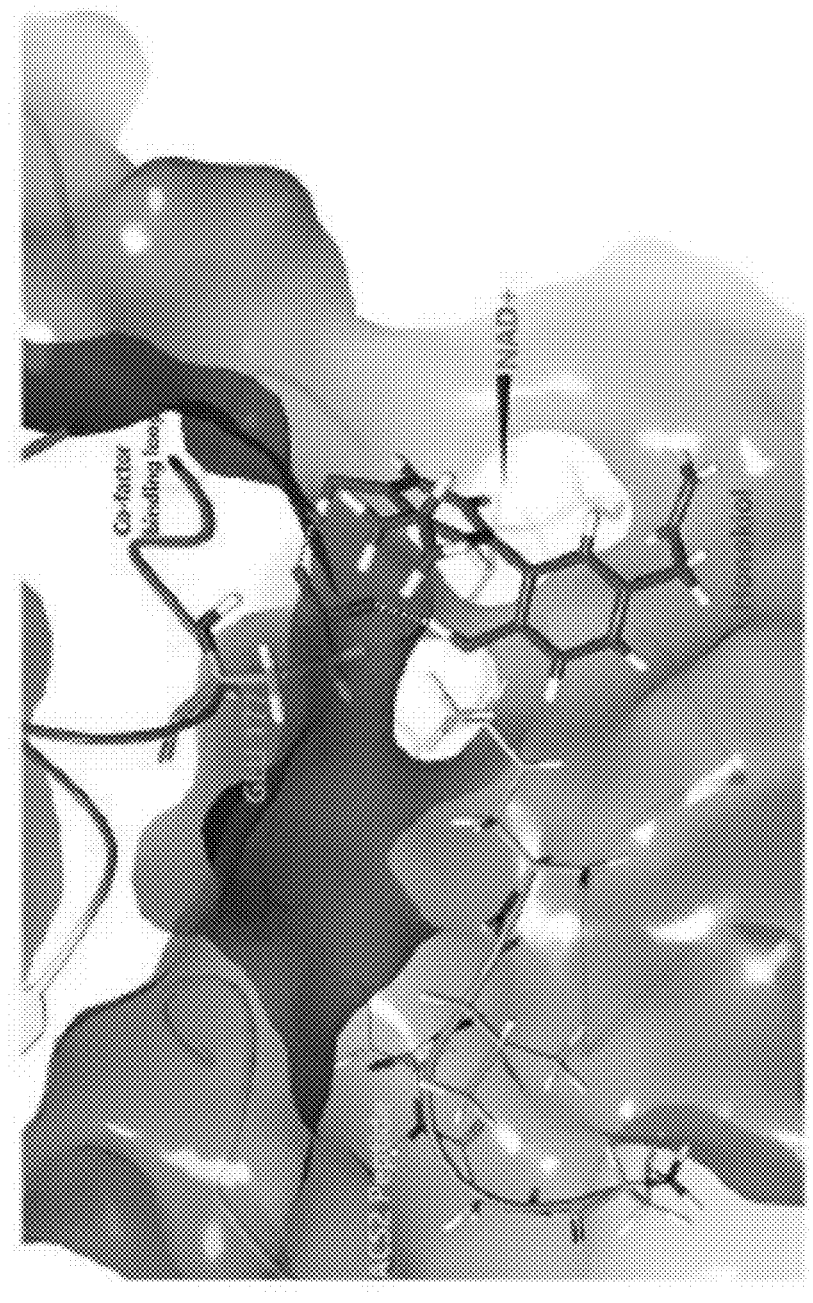
Figure 4A:
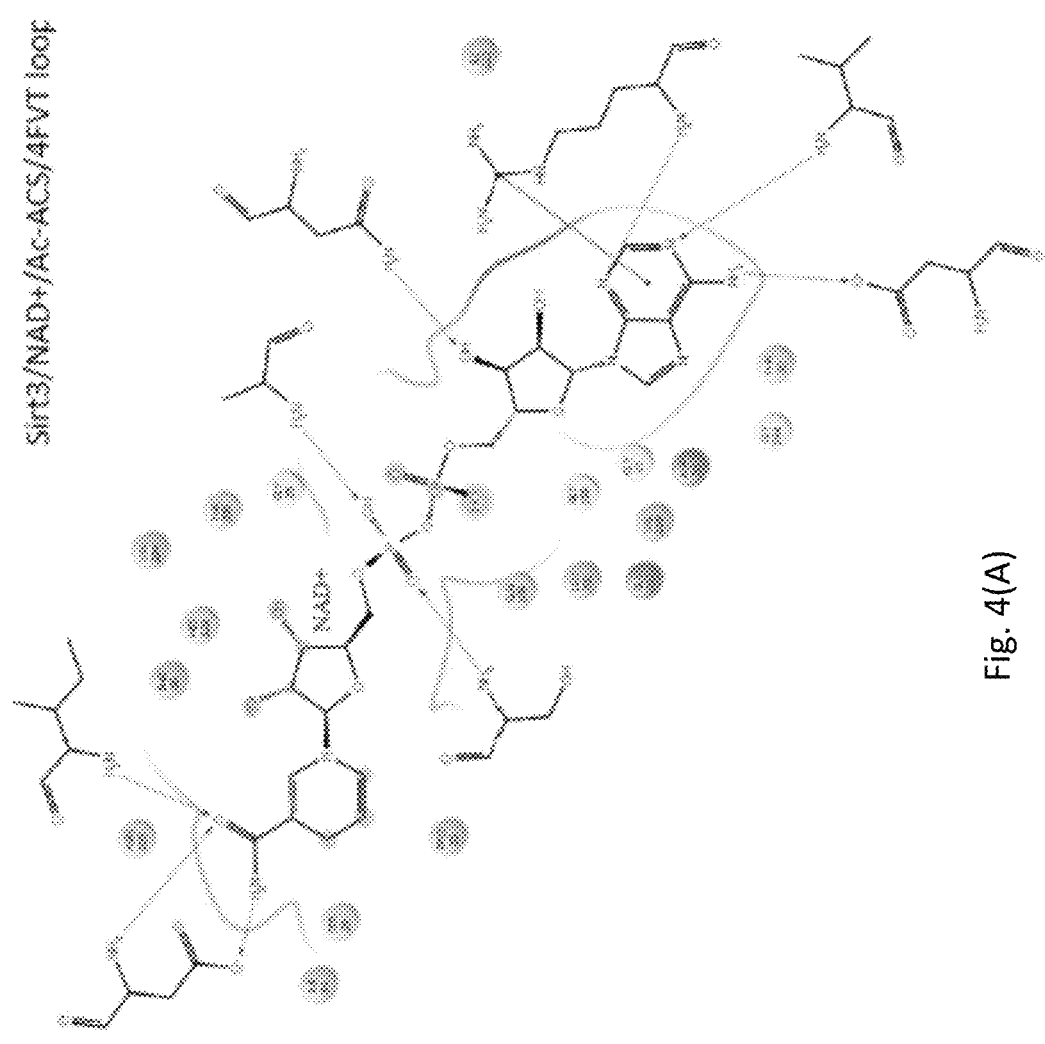
FIGS. 4(A)-4(B)—NAD$^+$ ligand interaction diagrams for the SIRT ternary reactants complex with FIG. 4(A) open and FIG. 4(B) closed loop conformations depicting the significant changes in the residue interactions with NAD upon closing of the loop induced by modulators. Geometries depicted are MD averages.
Figure 4B:
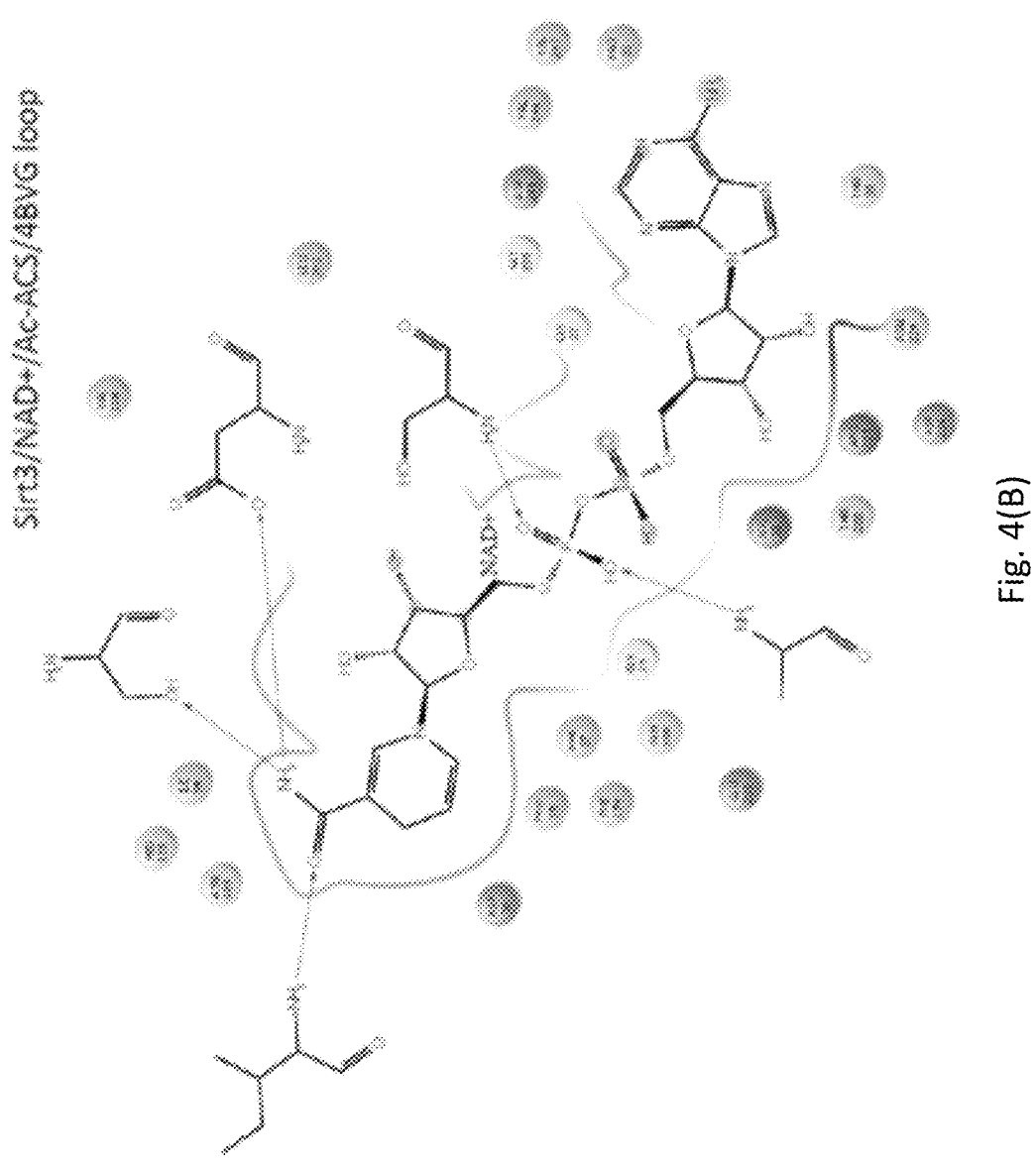

Honokiol (HKL) has been reported as a SIRT3 activator for the MnSOD protein substrate. Since SIRT3 does not possess a known allosteric site, HKL was studied as a potential hit compound for mechanism-based activation of SIRT3. The binding mode of HKL to human SIRT3 was investigated computationally through protein-ligand docking (FIG. 3) to the SIRT3:NAD$^+$:AcPr ternary reactants complex (prepared through molecular dynamics and QM/MM geometry optimization), which demonstrated high affinity (−5.8 kcal/mol) co-binding of HKL to a pocket above the active site. Docking predicts that HKL engages in hydrogen bonds with Glu 177 of the cofactor binding loop, which will induce conformational changes due to the loop's flexibility. (Nonpolar interactions are also observed with hydrophobic residues, including Val 348, that form part of the HKL binding pocket.) Docking of additional HKL derivatives to alternate loop conformations also showed H-bonding interactions with residues in the cofactor binding loop (data not shown). As such, we compared the interactions between the loop and NAD$^+$ based on molecular dynamics simulations for two different conformations of the cofactor binding loop in the ternary reactants complex—the open and closed loop conformations (FIG. 4). Whereas cationic residues including Arg 38 engage in favorable electrostatic interactions with NAD$^+$ upon loop closure, Phe 157 (shown in FIG. 1) induces strain in the nicotinamide moiety of NAD$^+$, which typically prevents loop closure in the absence of a modulator.

Figure 5A:
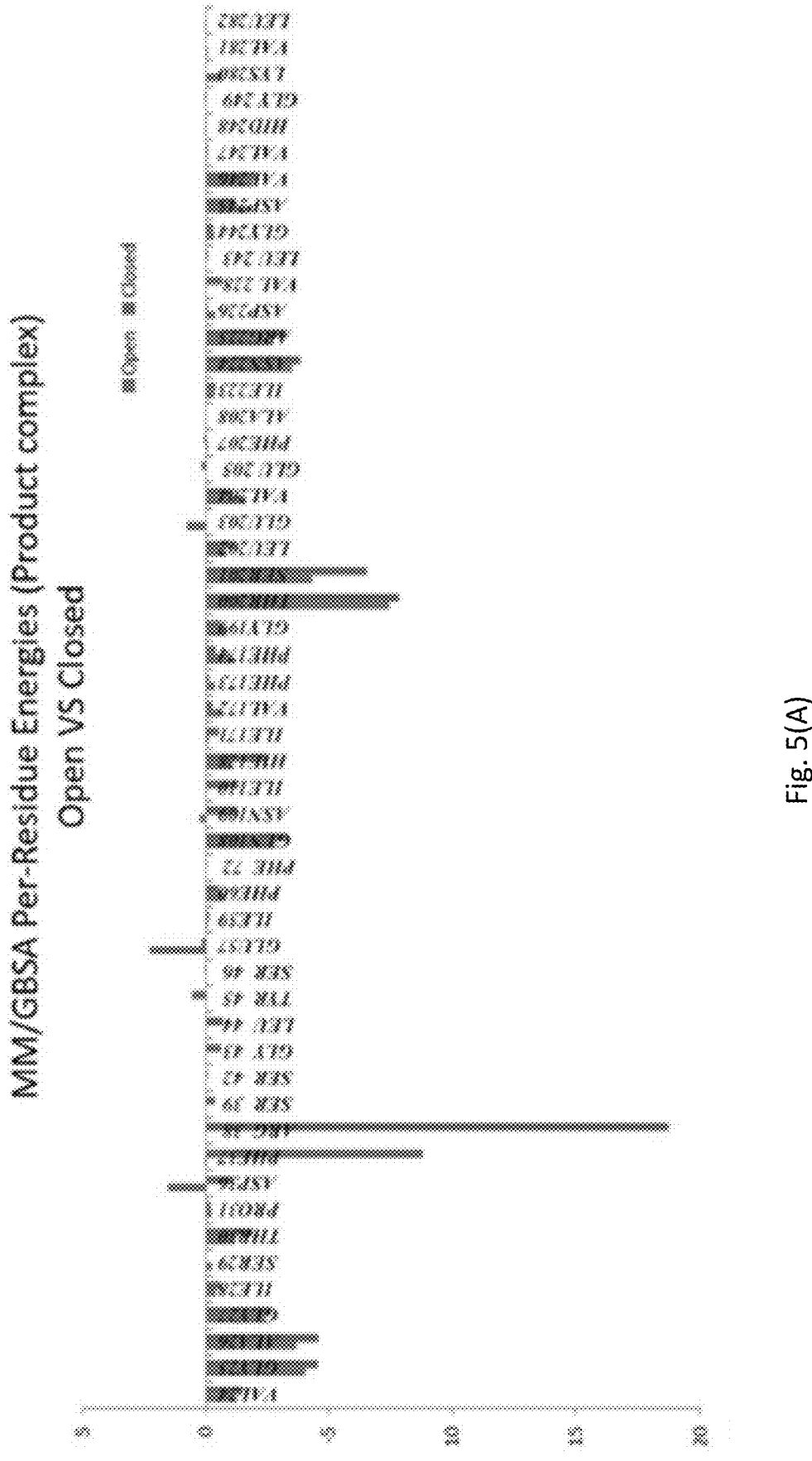
FIGS. 5(A)-5(B)—By-residue FIG. 5(A) MM-GBSA binding energies and FIG. 5(B) MM-PBSA MD average binding affinities of SIRT3 to the AADPR coproduct for open vs closed loop conformations.
Figure 5B:
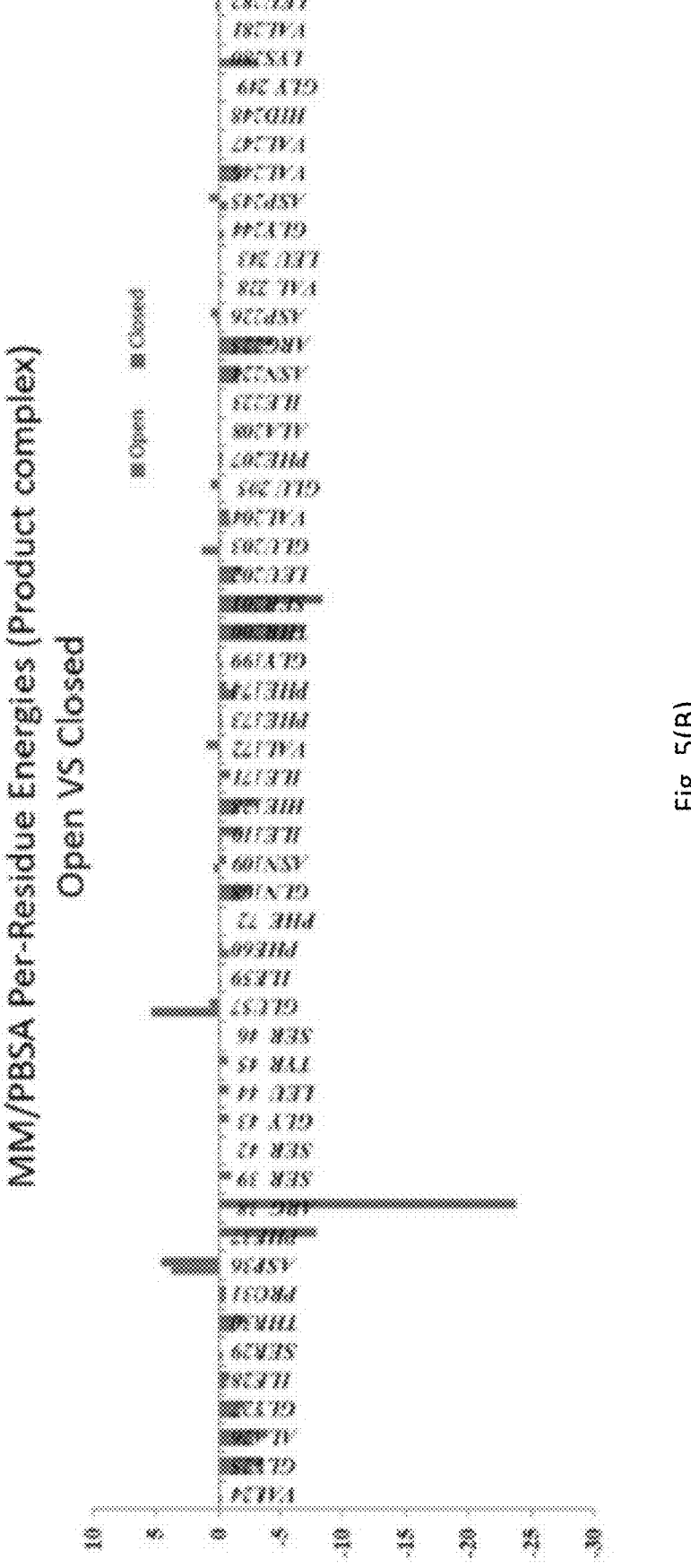

In addition, in order to investigate the effect of HKL-induced changes of the cofactor binding loop conformation on coproduct binding affinity, we calculated O-AADPR binding affinities from molecular dynamics simulations for open and closed conformations of the loop (FIG. 5). The significantly higher binding energies for the closed loop conformation demonstrate that stabilization of the closed loop conformation will increase coproduct binding affinity and reduce the rate of coproduct dissociation.

A 1.2 million small molecule screening library comprised of drug-like compounds was obtained from Chembridge. AWS cloud servers were applied for parallel batch docking for virtual screening. Two QM-MM geometry optimized SIRT3 complexes were used as receptors for docking tasks. The hit compounds were generated based on ranking of AUTODOCK VINA docking scores for the two receptors as well as H-bond interactions with relevant flexible degrees of freedom, including those in the cofactor binding loop. Honokiol was included in the library and identified as a hit compound according to these criteria.

II. Experimental Validation and Characterization of Hit Compounds for Nonallosteric Sirtuin Activation In this section, proposed sirtuin-activating compounds are experimentally characterized within the context of a mechanistic model, evaluating their characteristics within the context of the ideal features of mechanism-based activators. Both thermodynamic and kinetic measurements are made in order to characterize the equilibrium and steady state constants entering the mechanism-based enzyme activation model. We begin with the kinetic measurements.

Figures 6A, 6B:
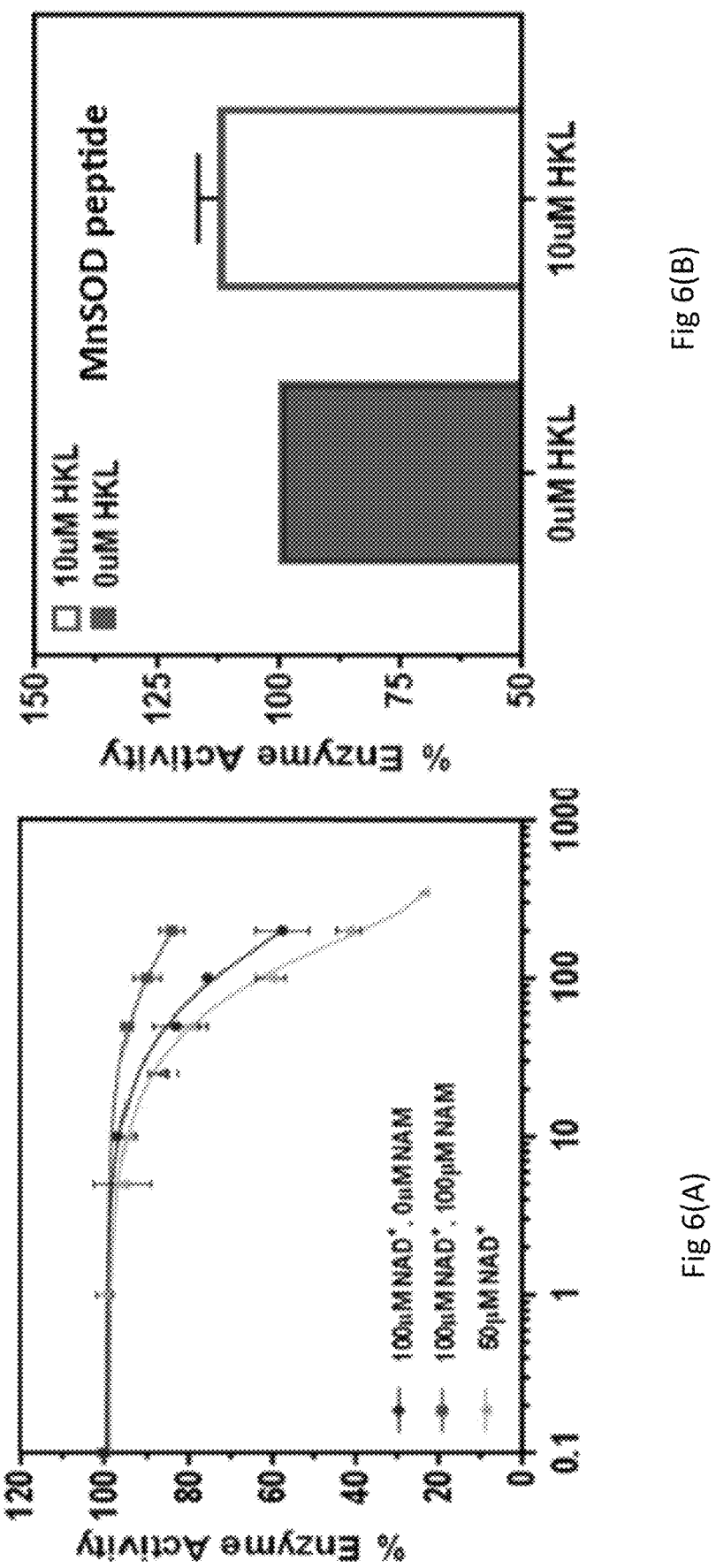
FIGS. 6(A)-6(D)—Effect of HKL on Sirt3 deacetylation activity using a label-free assay: steady state dose-response and non-steady state activation. Dose-response curves were measured under conditions where [E]$_0$/[S]$_0$<<1, where [S]$_0$ denotes the initial concentration of the limiting substrate, in order to maximize the contribution the steady state phase of the reaction to the curve. The lines are the results of global fitting; the lines were not fit independently to the data points in the individual panels. The error bars that are not visible are too small to view at this scale.
Figure 6D:
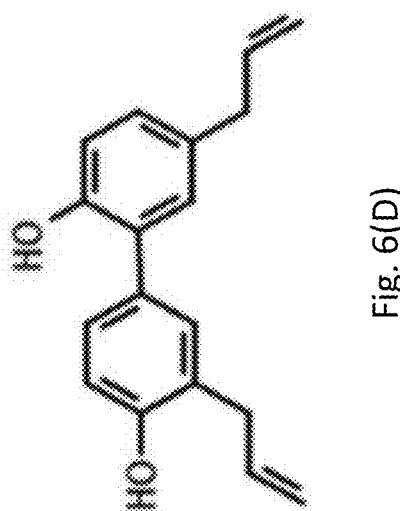
Figure 6C:
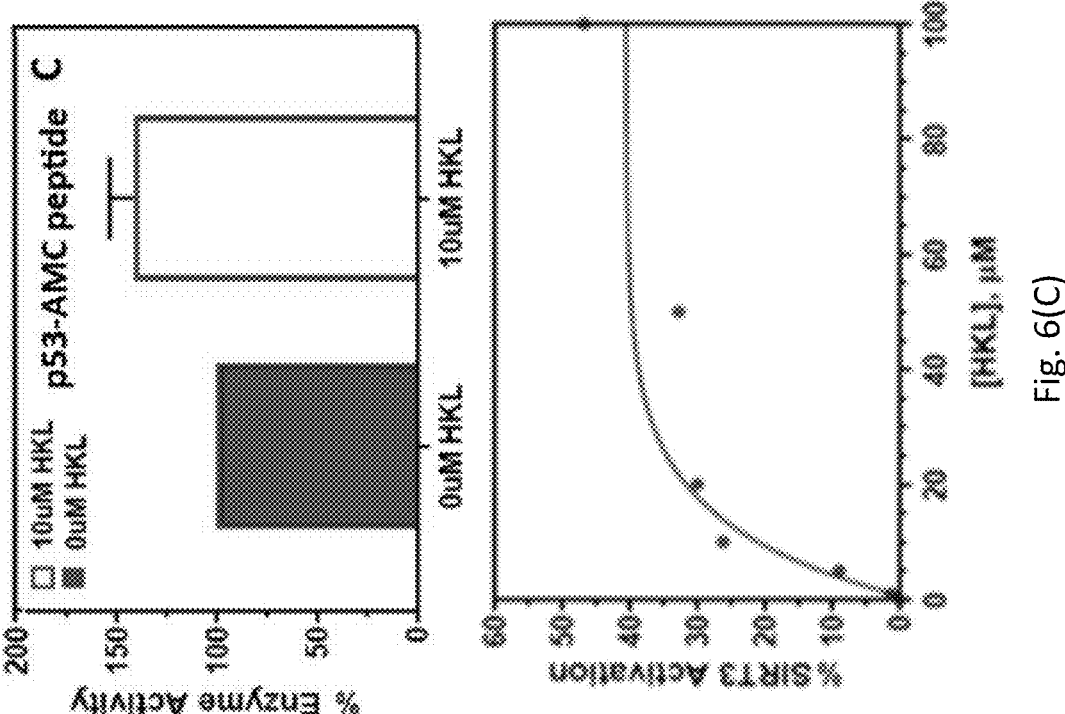

Kinetic characterization of HKL's effect on SIRT3 activity was carried out according to the principles of mechanism-based enzyme activation. First, top ranked compounds from the computational screen were assayed for non-steady state rate enhancement by measuring the extent of deacylated product formation at times prior to the achievement of the steady state. This was achieved by either measuring product formation at small times (FIGS. 6B and 6C, top) or employing a high ratio of enzyme to limiting substrate concentration such that the steady state was achieved later (FIG. 6B bottom, $[E]_0/[S]_0=0.3$). Full dose-response curves were then measured for compounds that displayed activation (FIG. 6C bottom). (Subsequently, dose-response curves were also measured at $[E]_0/[S]_0\ll1$, where $[S]_0$ is the initial concentration of the limiting substrate (NAD$^+$ or peptide) (FIG. 6A, FIGS. 19(A)-19(C)). FIGS. 6A and B illustrate how for $[E]_0/[S]_0<1$, which is required for steady state characterization, where S is the limiting substrate, the measurement time has a significant impact on the effect of HKL on enzyme activity, with activation occurring at short times (pre-steady state). Both the green curve in FIG. 6A and the bar plot in FIG. 6B were assayed at 50 uM NAD, but at significantly different times (30 min and 1.5 min, respectively). The red curve in FIG. 6A and the bar plot in FIG. 6B were assayed at progressively shorter times (10 min and 1.5 min respectively), but at different concentrations ofNAD+ and NAM, which affect the duration of the pre-steady state phase of the reaction. The observed activation of SIRT3 by HKL in FIG. 6B is highly statistically significant, with p<==0.001.

FIG. 6C in depicts how HKL also activates SIRT3 under non-steady state conditions for the p53-AMC peptide substrate, analogously to the results in FIG. 6B for the MnSOD substrate. This fluorolabeled substrate can be employed using the reaction conditions depicted in this Figure to rapidly screen for hit compounds that nonallosterically activate SIRT3 due to the sensitivity fluorescence-based activity assays. Activity assays with the fluorolabeled p53 substrate were repeated with HPLC (FIGS. 19(A)-19(C)) to eliminate the possibility of false positives.

The steady state rate of deacylation can be expressed as:

$$\frac{v}{v_{max}} = \frac{[NAD^+]\left(1+\frac{[NAM]}{K_1}\right)}{K_{m,NAD+}\left(1+\frac{[NAM]}{K_2}\right)+[NAD^+]\left(1+\frac{[NAM]}{K_3}\right)} \quad (1)$$

The steady state rate measurements at multiple values of $[NAD^+]$ and $[NAM]$ were carried out in order to estimate the parameters in this model.

Figures 7A, 7B:
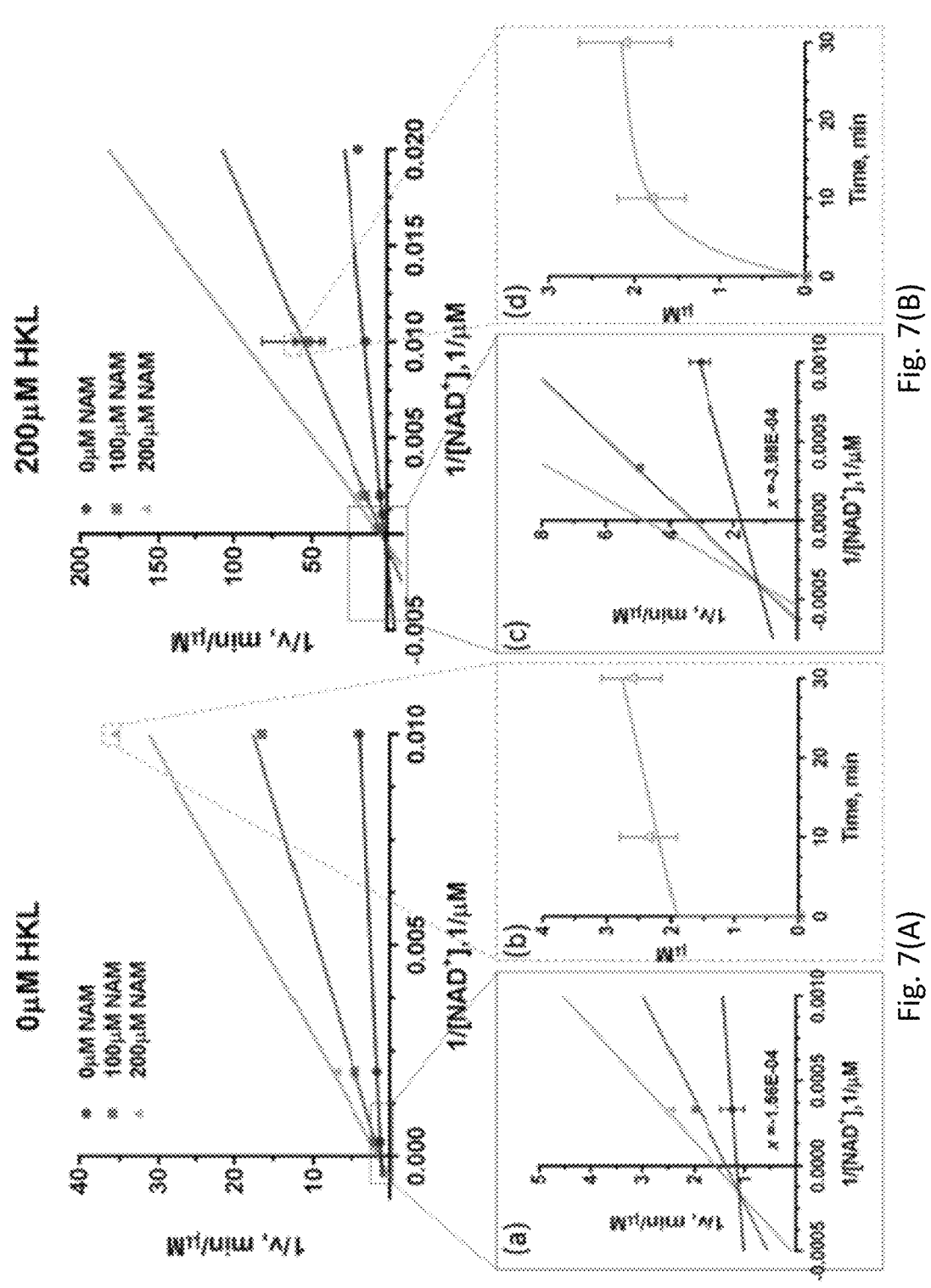
FIGS. 7(A)-7(B)—Steady-state kinetic characterization of deacetylation in the presence and absence of the mechanism-based modulator HKL. Double reciprocal plots for deacetylation initial rate measurements of saturating substrate peptide (MnSOD $K_{122}$) in the presence of different concentrations of NAM in FIG. 7(A) 0 µM HKL.
Figures 8A, 8B:
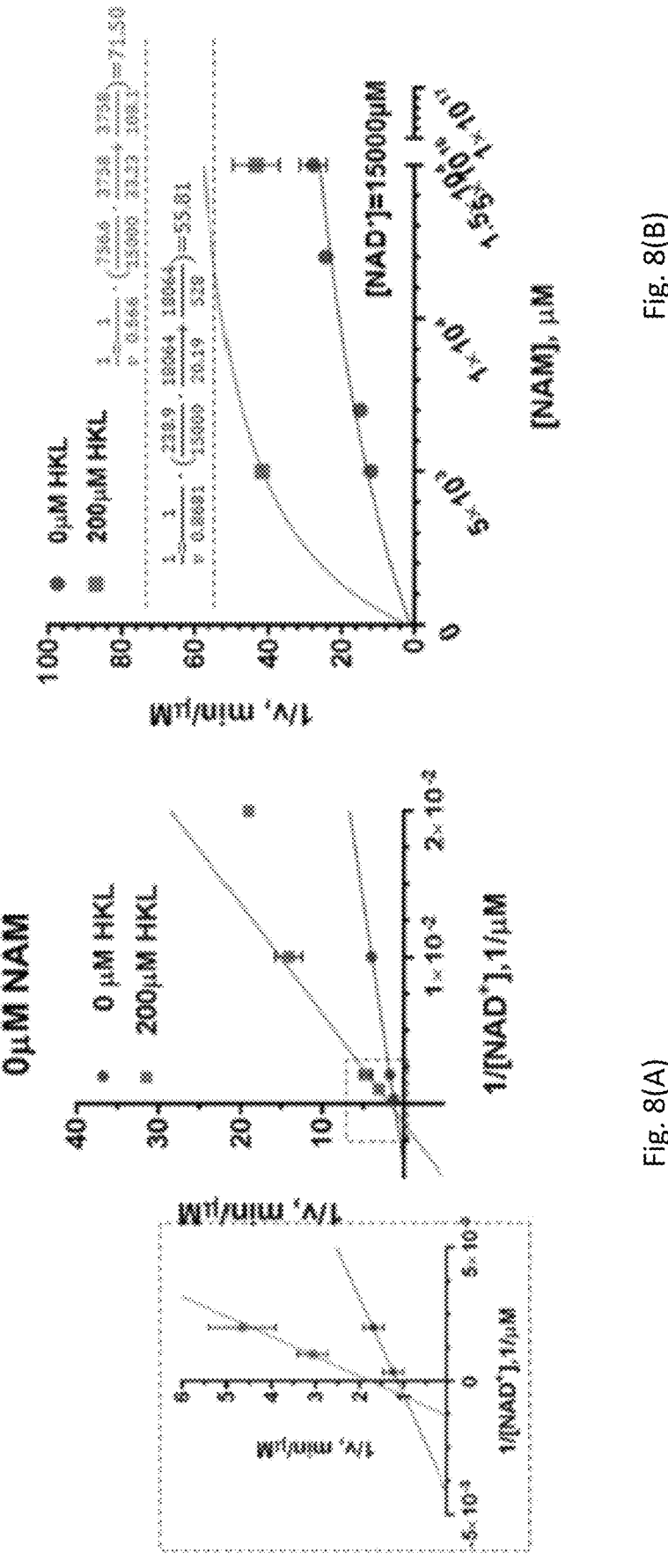
FIGS. 8(A)-8(D)—Non-allosteric modulation of hSirt3[102-399] deacetylation of MnSOD substrate: effect of $NAD^+$ and NAM.

The steady state results for the MnSOD substrate are presented in FIGS. 7, 8, and Table 1. The purpose of this study is to compare the observed changes in the steady state parameters $v_{max}$, $K_{m,NAD+}$, $K_1$, $K_2$, $K_3$ at 200 μM concentration (approximately saturating) to the changes conducive to activation that were delineated in reference. Note that at very high values of $[NAM]$, the effect of differences in $K_{d,NAM}$ induced by the modulator becomes negligible, allowing isolation of differences in the NAD$^+$ binding and ADP ribosylation/base exchange kinetics.

The insets in FIG. 7 show examples of the time series data collected (not the complete time series). These insets demonstrate that deacylation of this substrate displays a two phase behavior (pre-steady state/steady state phase) with a relatively slow first phase. Due to this behavior, a two-phase rather than one-phase exponential time series fitting was used. Irrespective of the first phase time constant, the rate in the second phase is almost identical. Hence the uncertainty in steady state rates is very low. The rate is generally almost constant over the measured times in the second phase.

Because of the apparent two-phase time series dynamics of catalysis for MnSOD, the relative amounts of product formation in the presence vs absence of HKL depends on the choice of measurement time, with a closer correspondence at lower times. In particular, in the presence of 100 μM NAM, which is on the same order of the magnitude as the physiological concentration of NAM, the amounts of product formed at 0 and 200 μM HKL after 10 mins are quite close (FIG. 6A). The pre-steady state and steady state phases of deacylation are further analyzed both experimentally and numerically below.

TABLE 1

| Model parameter estimates from global nonlinear fitting of Eq. (1) for SIRT3 in the presence and absence of 200 μM (saturating) HKL. $[E_0]$ = 1.85 μM | | |
|---|---|---|
| | 0 μM HKL | 200 μM HKL |
| $V_{max}$, μM/min | 0.8681 ± 0.012 | 0.566 ± 0.053 |
| $K_1$, μM | 18064 ± 8279 | 3758 ± 1572 |
| $K_m$, μM | 238.9 ± 12.92 | 756.6 ± 138.8 |
| $K_2$, μM | 20.19 ± 1.612 | 33.23 ± 6.886 |
| $K_3$, μM | 528 ± 105 | 108.1 ± 28.98 |
| Goodness of Fit | | |
| Degree of Freedom | 11 | 10 |
| R square | 0.9988 | 0.9947 |
| Absolute Sum of Squares | 0.001052 | 0.0006615 |
| Sy · x | 0.009782 | 0.008133 |

III. Measurement of Binding Affinities

Figure 9B:
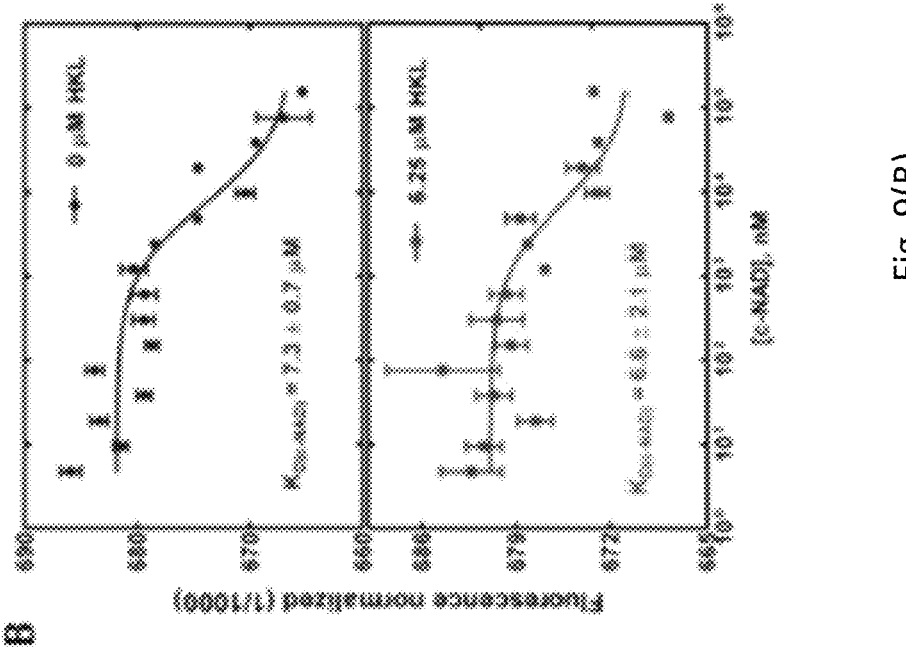
FIGS. 9(A)-9(D)—Binding affinity measurements for complexes in the sirtuin reaction mechanism.
Figure 9A:
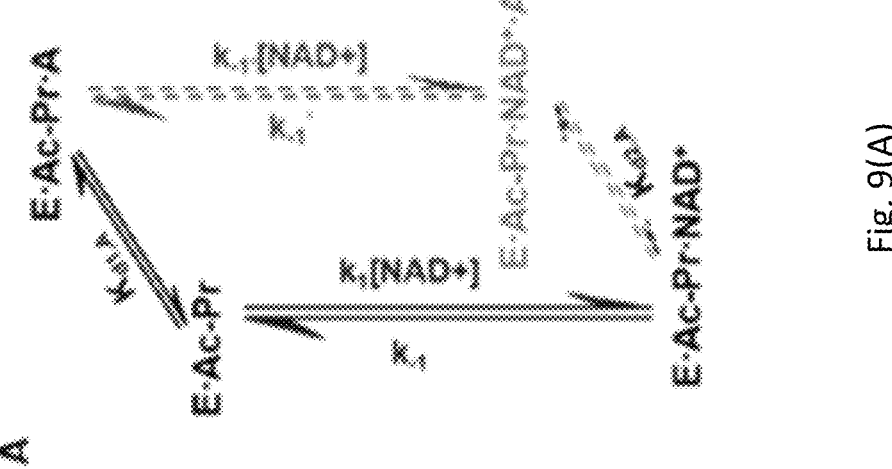
Figures 9C, 9D:
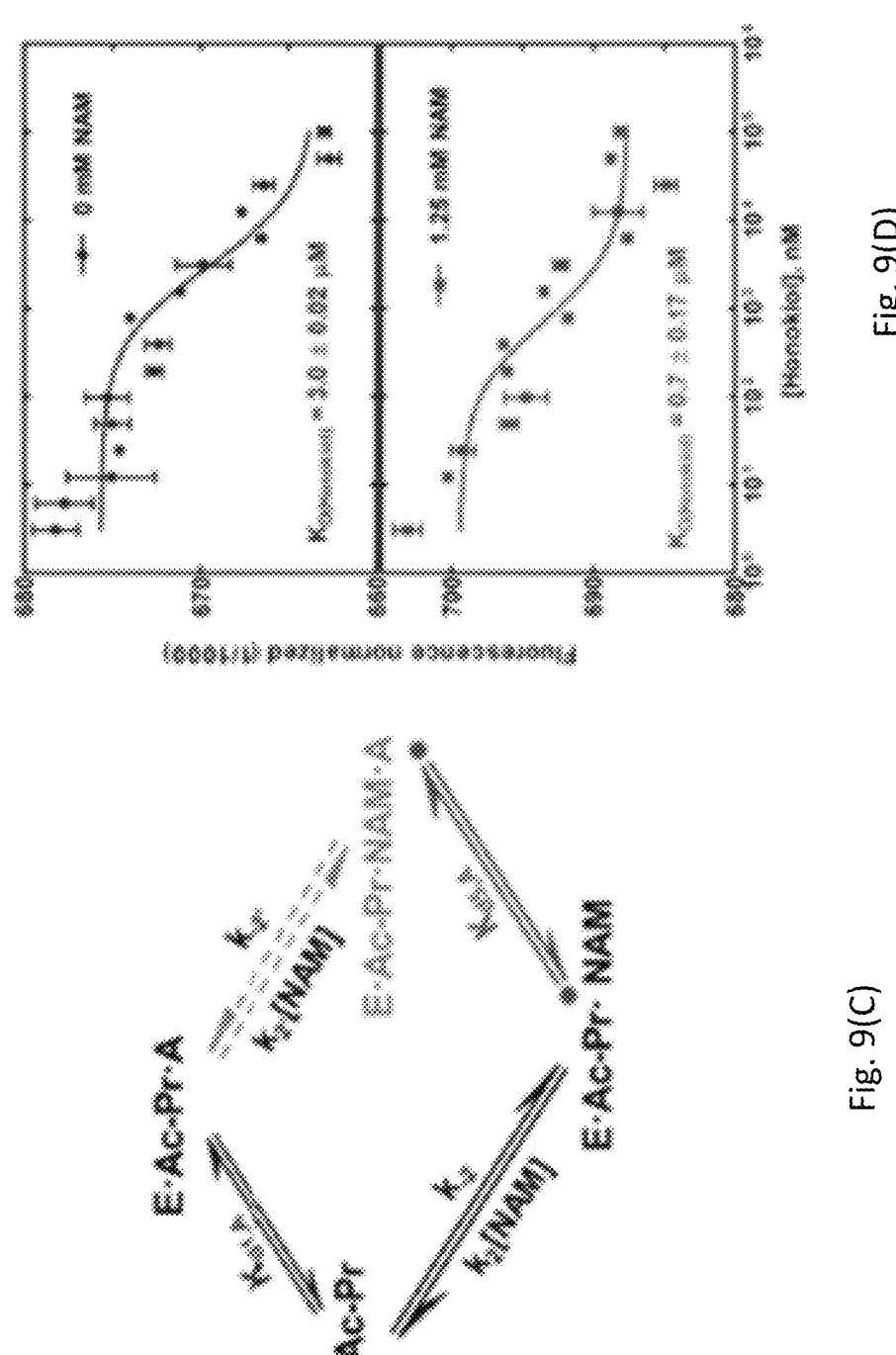
Figures 10A, 10B, 10C:
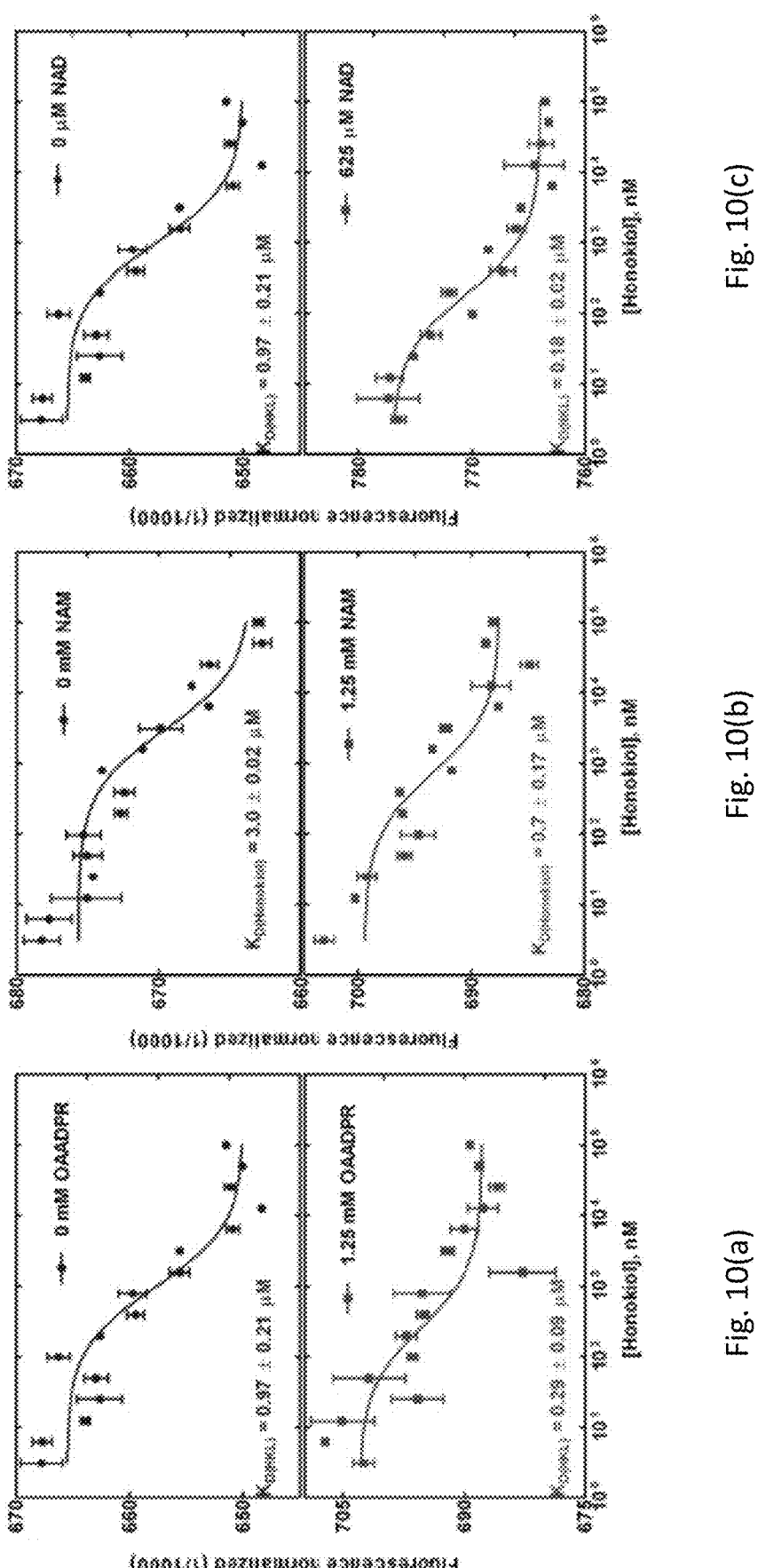
FIGS. 10(A)-10(C)—Binding affinity measurements of FIG. 10(A) Honokiol binding in the product complex: effect of 2'-O-acetylated ADP ribose coproduct.

The binding affinities of ligands to complexes in the catalytic mechanism of SIRT3/MnSOD peptide substrate were measured using microscale thermophoresis (MST; FIG. 9, FIG. 10). In order to carry out binding affinity measurements on the reactive complex of enzyme, acylated peptide substrate and NAD$^+$, the catalytically inert molecule carba-NAD$^+$ was synthesized and used this NAD$^+$ analog for those MST studies.

In addition to measuring the effect of HKL on NAD$^+$ binding affinity, we measured its effect on acylated peptide binding affinity, NAM binding affinity in the presence of acetylated peptide, deacylated peptide binding affinity, O-acetylated ADP ribose binding affinity in the presence of deacylated peptide (i.e., the product complex), and NAD binding affinity in the presence of deacylated peptide. The latter measurements in the presence of deacylated peptide were made in order to determine whether product inhibition plays any role in the observed kinetics.

In particular, the binding affinities of HKL or carba-NAD were measured in the ternary complex and product complex. Cooperative binding between HKL and the relevant ligand were studied in each case. It was observed that HKL can have synergistic binding interactions with several ligands.

IV. Substrate Dependence of Nonallosteric Modulation

Figure 11B:
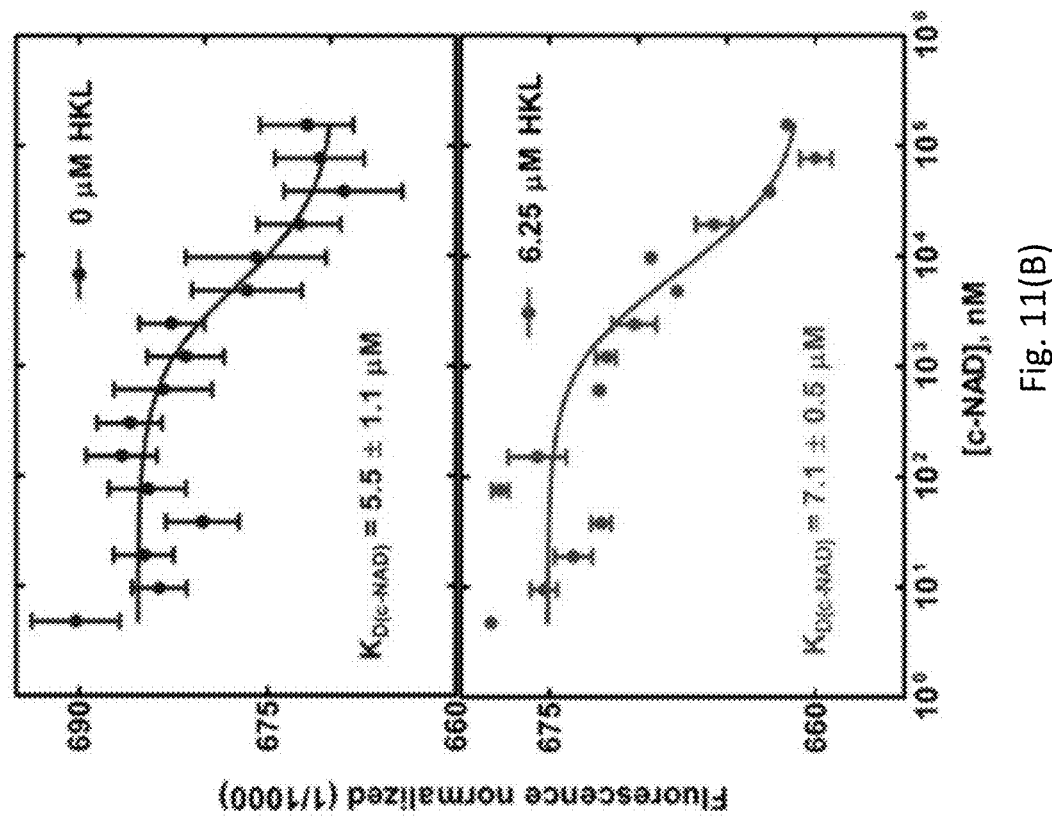
FIGS. 11(A)-11(B)—Binding affinity measurements of carba-NAD binding in the ternary complex of an alternate substrate: effect of HKL.
Figure 11A:
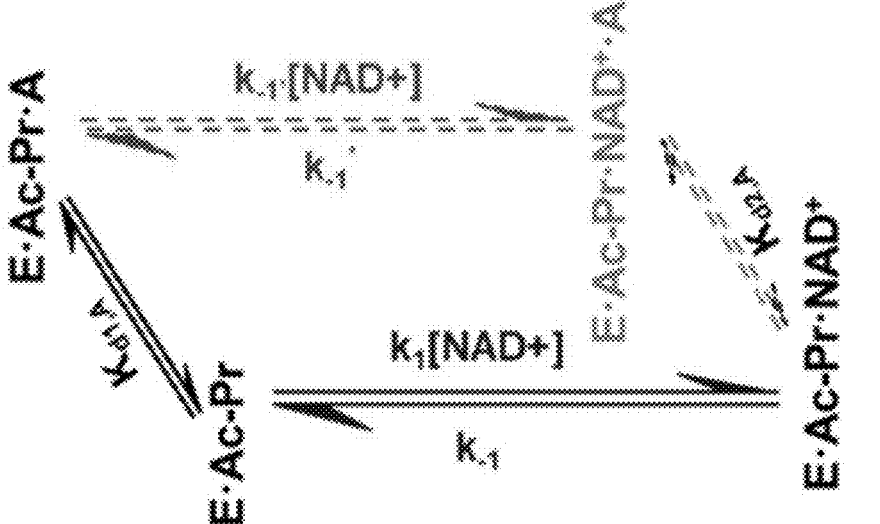

The p53-AMC substrate was studied in order to explore the substrate selectivity of modulation by HKL (FIGS. 11(A) and 11(B)). In enzyme design, the analogous problem of substrate specificity of an engineered protein is often considered. Due to the differing effects of the modulator on these two substrates, which can be identified and characterized within the present framework, substrate selectivity of nonallosteric activation can in principle be engineered.

Figures 11C, 11D:
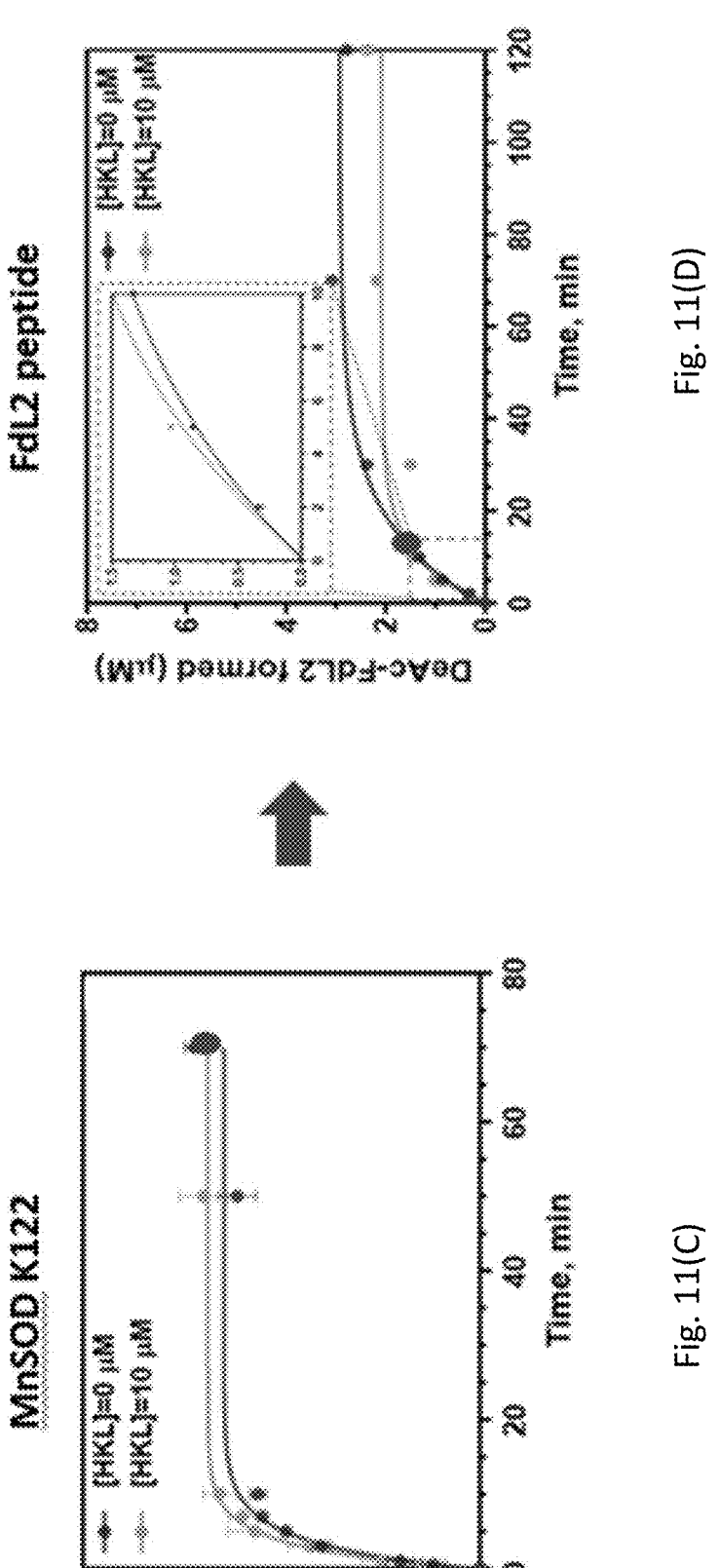
FIGS. 11(C)-11(D)—Sirt3 Activation by HKL.

For this substrate as well, HKL binding to catalytically active complexes (FIGS. 11(A) and 11(B)) and a slight $k_{cat}$ efficiency decrease in the presence of modulator were verified. MST measurements on carba-NAD$^+$ indicate a decrease in NAD$^+$ binding affinity (FIGS. 11(A) and 11(B)). Non-steady state activation by HKL in the presence of p53-AMC substrate was studied by direct measurements of activity under higher enzyme concentration ($[E]_0/[NAD^+]_0=0.3$) with unsaturated HKL. The results are reported in FIGS. 11(C) and 11(D). The activation was observed under non-steady state condition and inhibition effect was spotted under steady state condition.

V. Non-Steady State Activation of SIRT3 by Honokiol

Figures 12A, 12B:
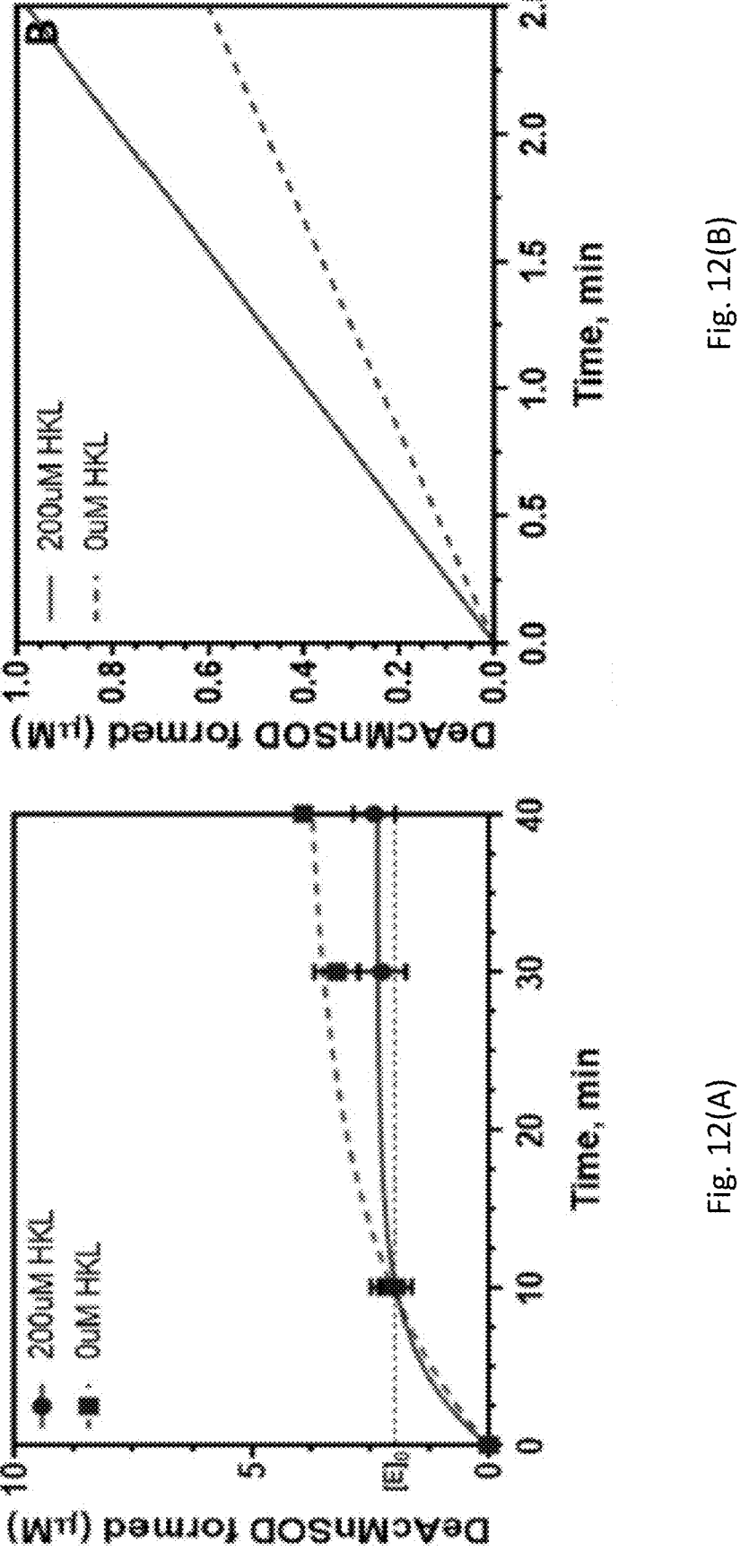
FIGS. 12(A)-12(D)—Effect of Honokiol on Sirt3 deacetylation activity: initial rate determination.
Figures 12C, 12D:
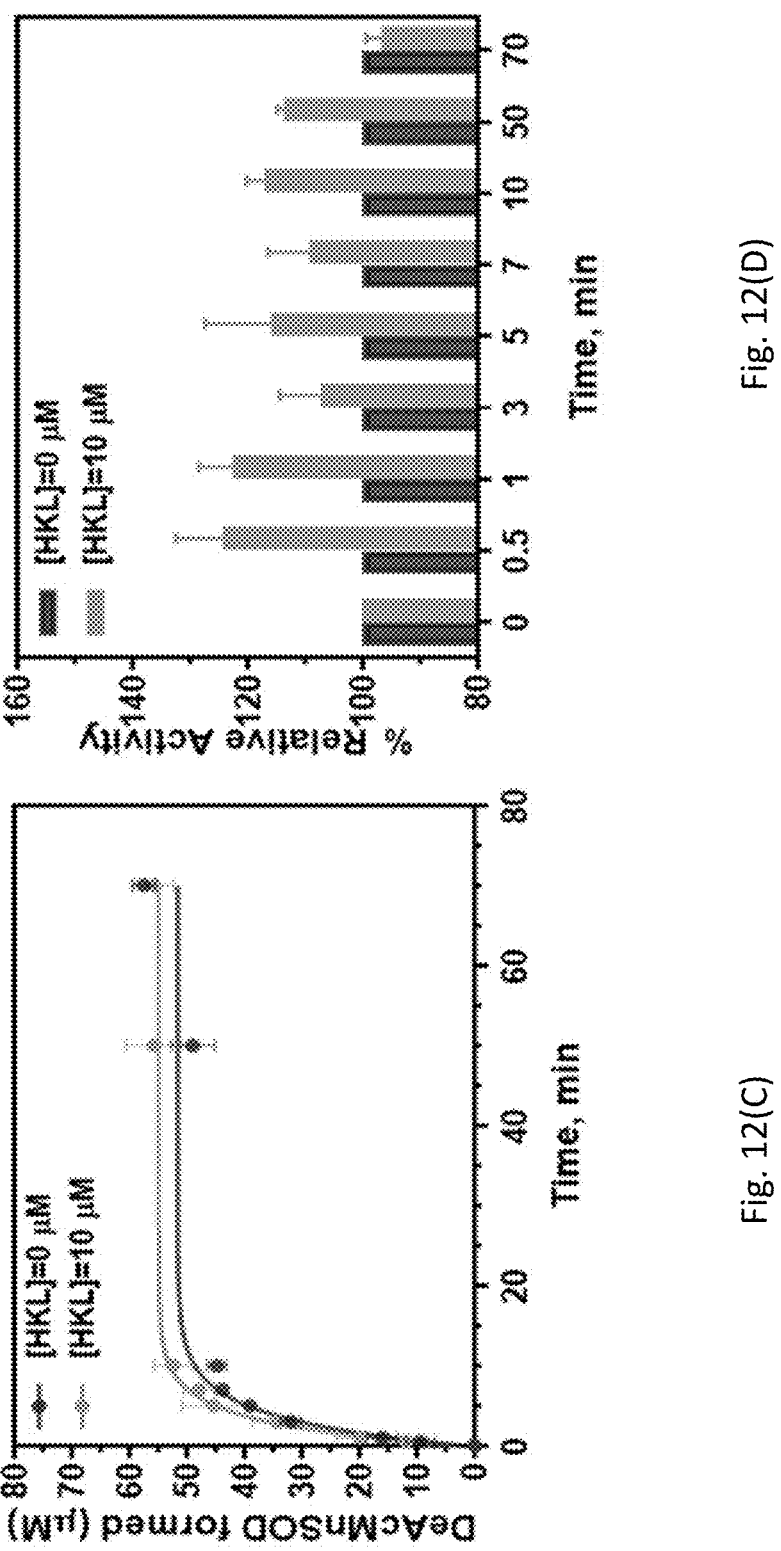

The initial rate of deacetylation of the MnSOD substrate was observed to increase in the presence of HKL (FIG. 12) This effect was observed under conditions where the initial rate of deacetylation was sufficiently low that the initial rate could be distinguished from the steady state rate.

A 0 to 40 minute time series fitting under these conditions captures the initial rate enhancement due to saturating HKL (FIG. 12A,B) whereas a longer time series enabled identification of pre-steady state and steady state phases, and accurate estimation of the steady state rate through double exponential fitting (FIG. 13) The transition between the pre-steady state phase (with HKL-induced activation) and steady state phase occurs after the concentration of deacetylated product exceeds the concentration of enzyme, i.e. after each enzyme molecule has catalyzed one reaction. This pre-steady state effect is also observed in the dose-response curve (FIG. 6A) at 100 μM NAD$^+$, 100 μM NAM ($[E]_0 <<$ $[S]_0$ conditions; note 100 μM NAM is on the same order of the magnitude as the physiological concentration of NAM).

Non-steady state activation by HKL was further explored through direct measurements of activity in the presence of unsaturating HKL (10 uM). The results are reported in FIG. 12C, D, which depict pre-steady activation of SIRT3-catalyzed deacetylation by HKL through measurements of product formation. While the data in FIG. 12A (and also the dose-response curves in FIG. 6A) were collected for the purpose of steady state analysis and characterization, the data in FIG. 12C, D (and FIG. 6B) were collected for pre-steady state analysis. As noted, the use of unsaturating [HKL](as in FIG. 12C, D) can facilitate activation, but saturating [HKL](as in FIG. 12A) is required for steady state parameter estimation in the presence of bound HKL. The standard errors of the activation (relative activity) in the presence of 10 uM HKL were reported in FIG. 6B above, with p<=0.001. Thus, honokiol is a non-steady state SIRT3 activator.

VI. Examples of Reported Hit Compounds Not Validated as Nonallosteric Activators Finally, another class of reported sirtuin activators— dihydropyridines, or DHPs were previously studied with only labeled assays that may be prone to false positives. The effects of these compounds on SIRT3 activity were studied using the p53-AMC substrate and two assays—both a fluorescence-based and an HPLC assay. The results suggest that DHPs are false positive compounds and not sirtuin activators. In addition, protein-ligand docking did not identify a high affinity binding site. Careful scrutiny should be applied to DHPs reported as activators, due to this finding and the autofluorescence of DHPs. The appropriate controls were applied in the current kinetic study of SIRT3-HKL with p53-AMC substrate, which eliminates the possibility of false positives.

VII. Numerical Simulation of Activation by Nonallosteric Hit Compounds

Figure 14:
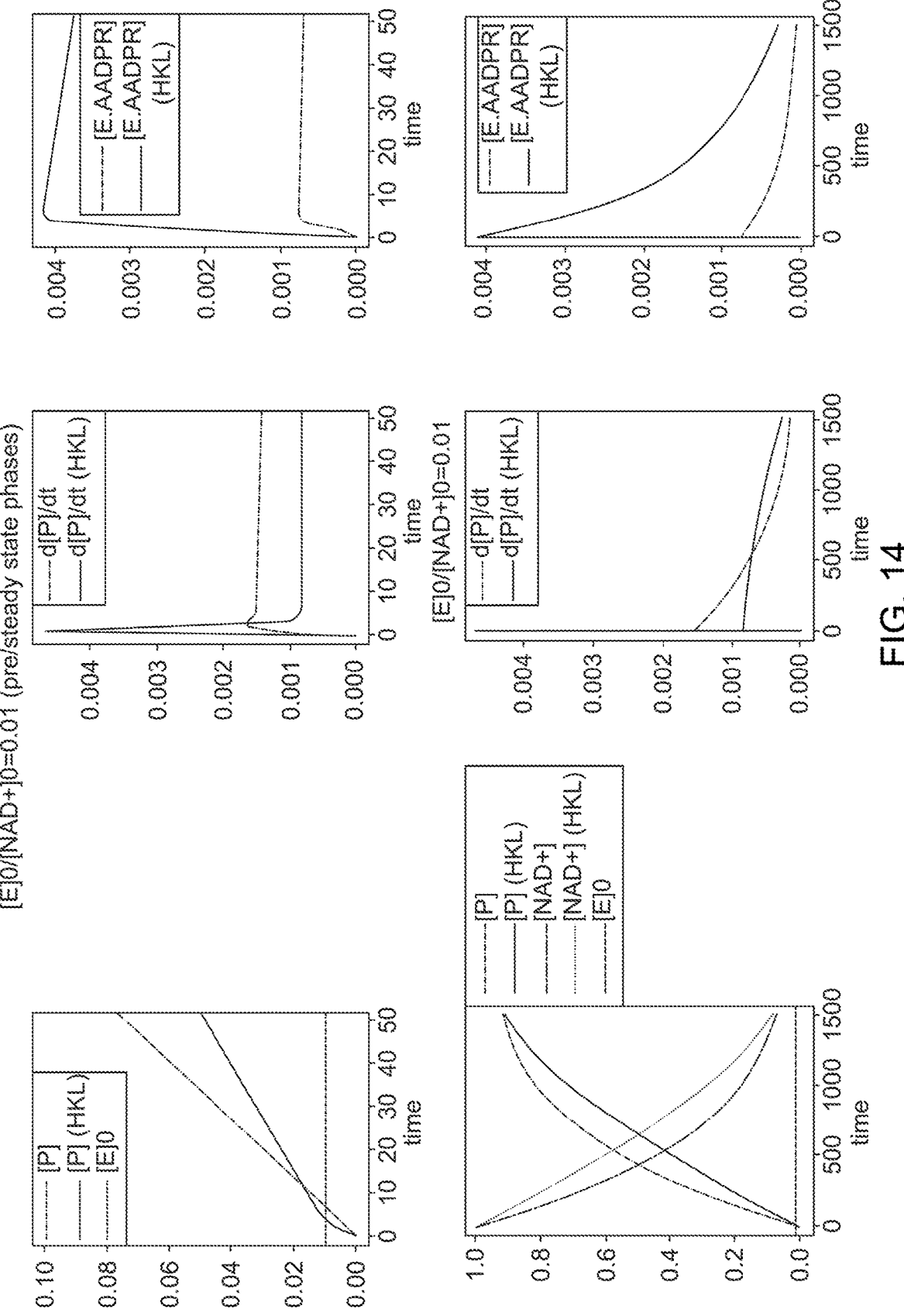
FIG. 14. Numerical simulations of the dynamics of SIRT3-catalyzed deacetylation under $[E]_0/[NAD^+]_0<<1$ conditions in the presence and absence of a non-steady state MB-STAC like HKL. Top: pre-steady state and steady state phases; Bottom: full reaction. P=deacetylated peptide product. Simulation parameters are defined in the text, and do not precisely correspond to the true parameter values for HKL.
Figure 15:
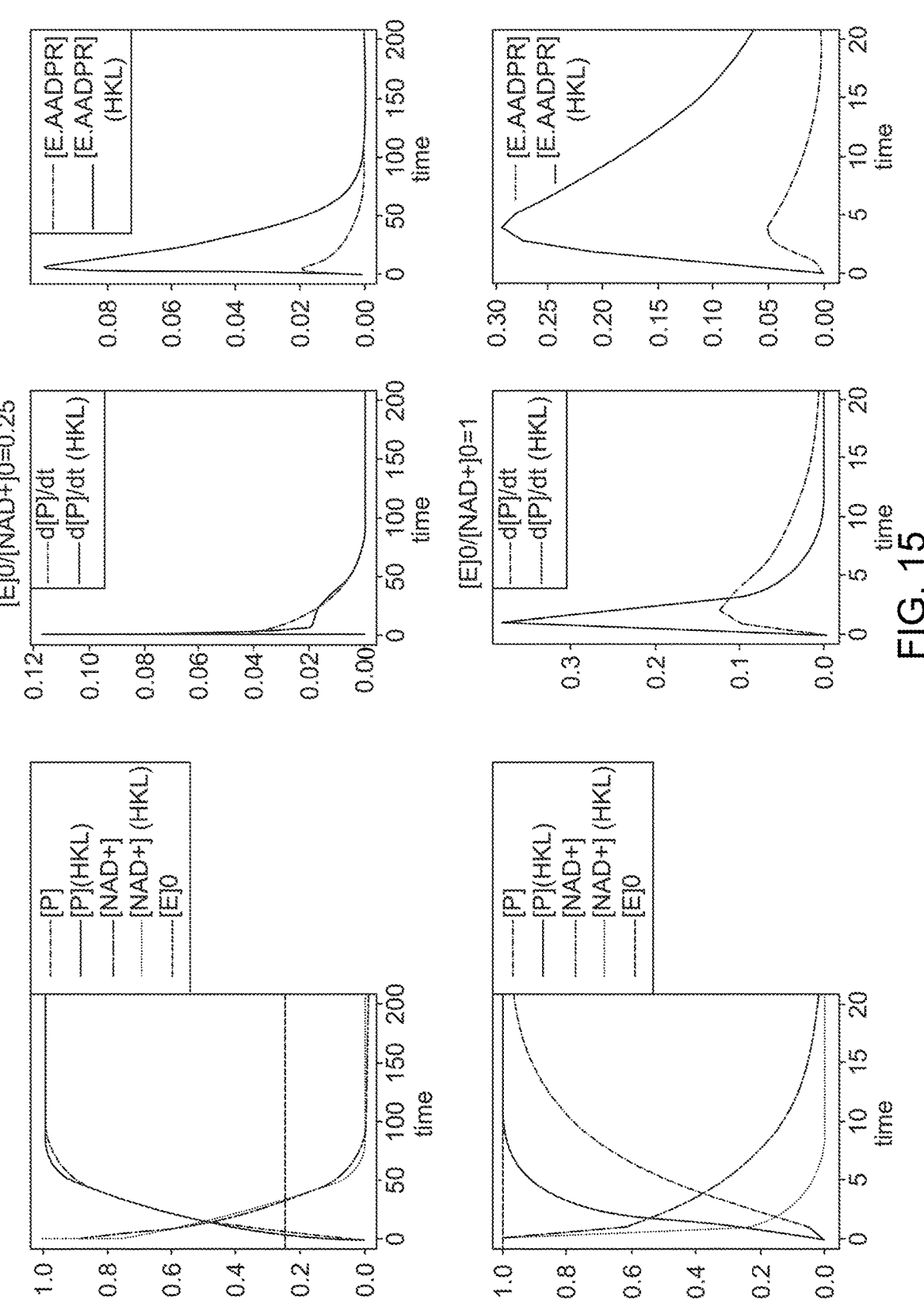
FIG. 15. Numerical simulations of the dynamics of SIRT3-catalyzed deacetylation under $[E]_0/[NAD^+]_0<1$ (top), =1 (bottom) conditions in the presence and absence of a non-steady state MB-STAC like HKL. P=deacetylated peptide product. Simulation parameters are defined in the text, and do not precisely correspond to the true parameter values for HKL.

As shown above, for the MnSOD substrate, HKL increases the binding affinity of NAD$^+$ in the SIRT3 ternary reactants complex, alters the base exchange equilibrium constant, and also increases the binding affinity of AADPR coproduct. This was shown to increase the pre-steady rate of deacetylation but not the steady state rate under saturating HKL. In order to efficiently analyze the net result of these effects on the dynamics of SIRT3-catalyzed deacetylation over the entire course of the reaction, we carried out numerical simulations of the reaction dynamics under multiple initial conditions including several $[E]_0/[NAD^+]_0$ at saturating AcPr, over all three phases of the reaction. In these simulations, the simplifying assumptions were applied that a) all ligands have equal off rates in the absence of HKL and NAD$^+$ has an on rate 10 times that of NAM; b) HKL increases the on rate of NAD$^+$ by a factor of five, increases the rate of ADP ribosylation by a factor of five, and reduces the off rate of AADPR by a factor of 10. The results are shown in FIGS. 14 and 15.

VIII. Analysis

The catalytic cycle of sirtuin enzymes proceeds in two consecutive stages. In the first stage (ADP-ribosylation), the NAM moiety of NADY is cleaved through nucleophilic attack of the protein substrate's acyl-Lys side chain to create a positively charged O-alkylimidate intermediate. NAM-induced reversal of the intermediate (the "base exchange" reaction) results in regeneration of NAD$^+$ and acyl-Lys protein. The thermodynamics of this reversible reaction affects both the potency with which NAM inhibits sirtuins as well as $K_{m,NAD+}$ (the Michaelis constant for NAD$^+$). Stage 2 of sirtuin catalysis includes the rate-determining step and involves four successive steps that conclude in deacylation of the protein substrate's Lys side chain and generation of the coproduct, 0-acetyl ADP ribose.

Using expression (1), it is possible to determine the initial rate of deacylation for specified intracellular concentrations of NAD$^+$ and NAM, if the rate constants are known. At constant [NAM], Eq. (1) is usually represented graphically as double reciprocal plots, where the slope of the plot (1/v vs 1/[NAD$^+$]) at [NAM]=0 is $K_{m,NAD^+}/v_{max}$, for which the expression is:

$$\frac{K_{m,NAD^+}}{v_{max}} = \frac{1}{[E]_0}\left(\frac{1}{k_1} + K_{d,NAD+}\frac{k_{-3}+k_{-2}}{k_{-3}k_2}\right) = \frac{K_{m,NAD^+}}{k_{cat}[E]_0} \quad (2)$$

The steady state parameter α, which measures the extent of competitive inhibition by NAM, the endogenous inhibitor, against the NAD$^+$ cofactor, can be written in terms of the ratio of $K_{d,NAD+}$ and $K_{m,NAD+}$:

$$\alpha = \frac{K_3}{K_2} \approx \frac{K_{d,NAD+}}{K_{m,NAD+}}\frac{K_{ex}}{1+K_{ex}} \quad (3)$$

where $K_{ex}=k_{-2}/k_2$.

For enzyme activation to be possible, the modulator must co-bind with NAD$^+$ and acylated peptide. Moreover, non-allosteric activators must bind in the vicinity of the active site and modulate local conformational degrees of freedom to enhance enzyme activity. In previous studies, we presented a theory of mechanism-based enzyme activation, for the purpose of developing a foundation for the characterization and design of nonallosteric enzyme activating compounds. This theory provides a unifying framework under which such compounds can be characterized and hits can be evolved into leads. Here, we apply this theory to experimental data we collected for HKL.

FIG. 16 provides the expressions for each of the modulated steady state constants in the presence of a specified concentration [A] of the hit compound, according to one mechanism-based enzyme activation theory. The $K_{dt,A}$ denote the dissociation constants of the hit compound with respect to the respective reaction intermediates indexed by i. These conditions establish the biophysical properties of the compound that are required to elicit changes in the steady state constants that are conducive to activation. A hit compound may be defined as one that satisfies a subset of the steady state conditions enumerated, and may also display activation under non-steady state conditions, which can reduce inhibitory effects of the compound that are observed under steady state conditions, as discussed further below.

IX. Characterization of HKL Modulation of SIRT3 Using Computational, Steady State Kinetic, and Thermodynamic Data Because nonallosteric modulators operate according to new modes of action, the traditional approach of characterizing a compound as uncompetitive, noncompetitive or competitive with respect to substrates is not sufficient, even if the modulator has a net inhibitory effect.

The data reported above indicate that HKL cobinds with the peptide substrate and cofactor of SIRT3. Under the conditions tested (saturating HKL), the net effect of SIRT3 on MnSOD peptide substrate was pre-steady state activation followed by steady state inhibition. The mechanistic model above is required to understand the effects of HKL on the kinetic parameters of the enzymatic reaction, explain HKL's activation of SIRT3 activity under physiological non-steady state conditions and evaluate the potential to improve HKL's activation of SIRT3 through hit-to-lead evolution.

The computational results in FIGS. 2-5 demonstrate that HKL cobinds with SIRT3 substrates near the active site and induces a change in the conformation of the cofactor binding loop due to the latter's flexibility. It is not an allosteric modulator. The induced changes in the cofactor binding loop conformation affect the binding of $NAD^+$ as well as that of the AADPR coproduct. This conformational change is predicted to have a significantly favorable effect on AADPR coproduct binding affinity (FIG. 5), whereas its effect on $NAD^+$ binding affinity is predicted to be less significant. Moreover, due to the interaction of the modulated loop conformation with the nicotinamide moiety of NAM (FIG. 4), the resulting change in $NAD^+$ binding geometry is expected to alter the base exchange rate constants of the reaction.

Figure 17:
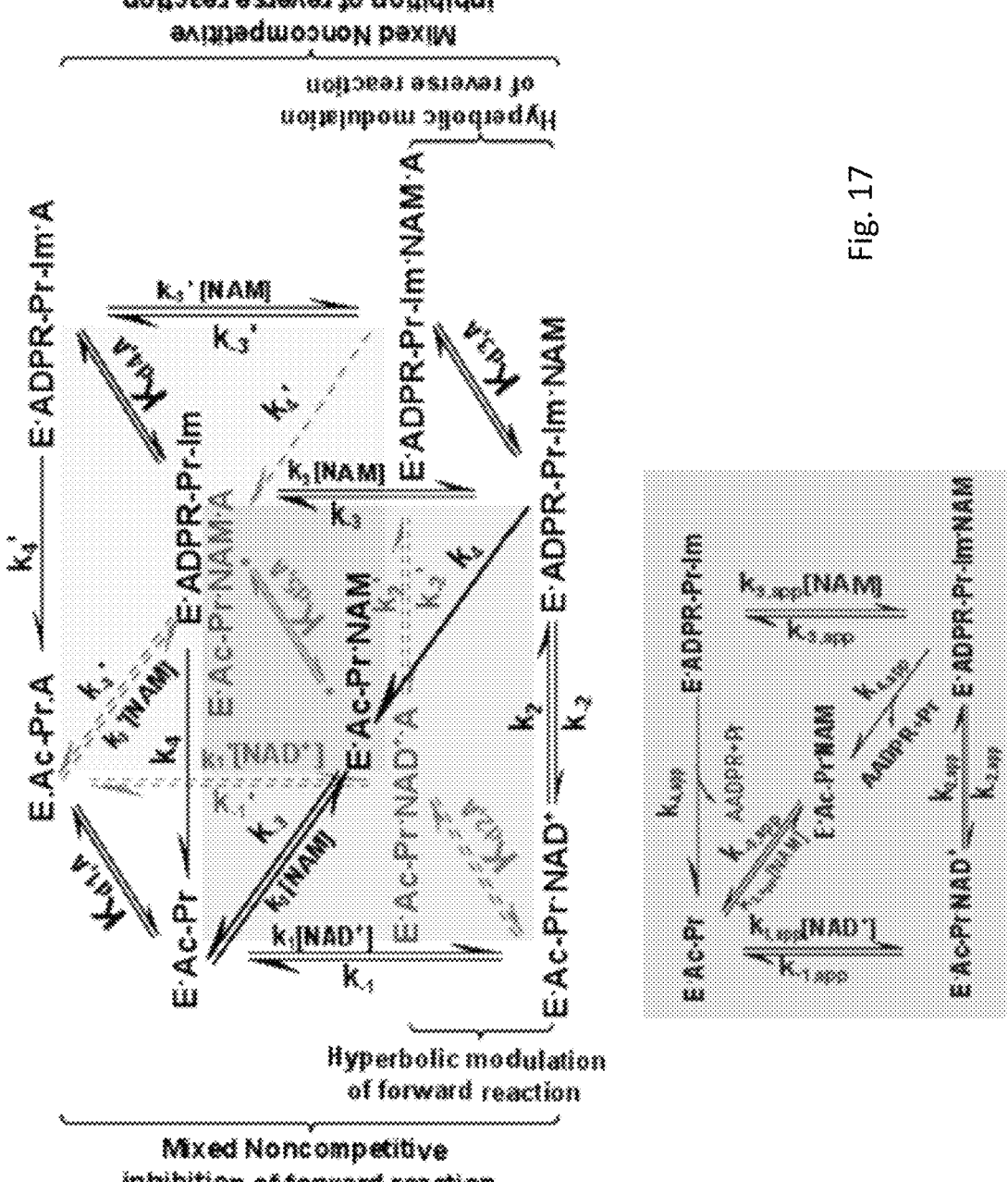
FIG. 17 illustrates a general model for mechanism-based sirtuin enzyme activation.
Figures 18A, 18B:
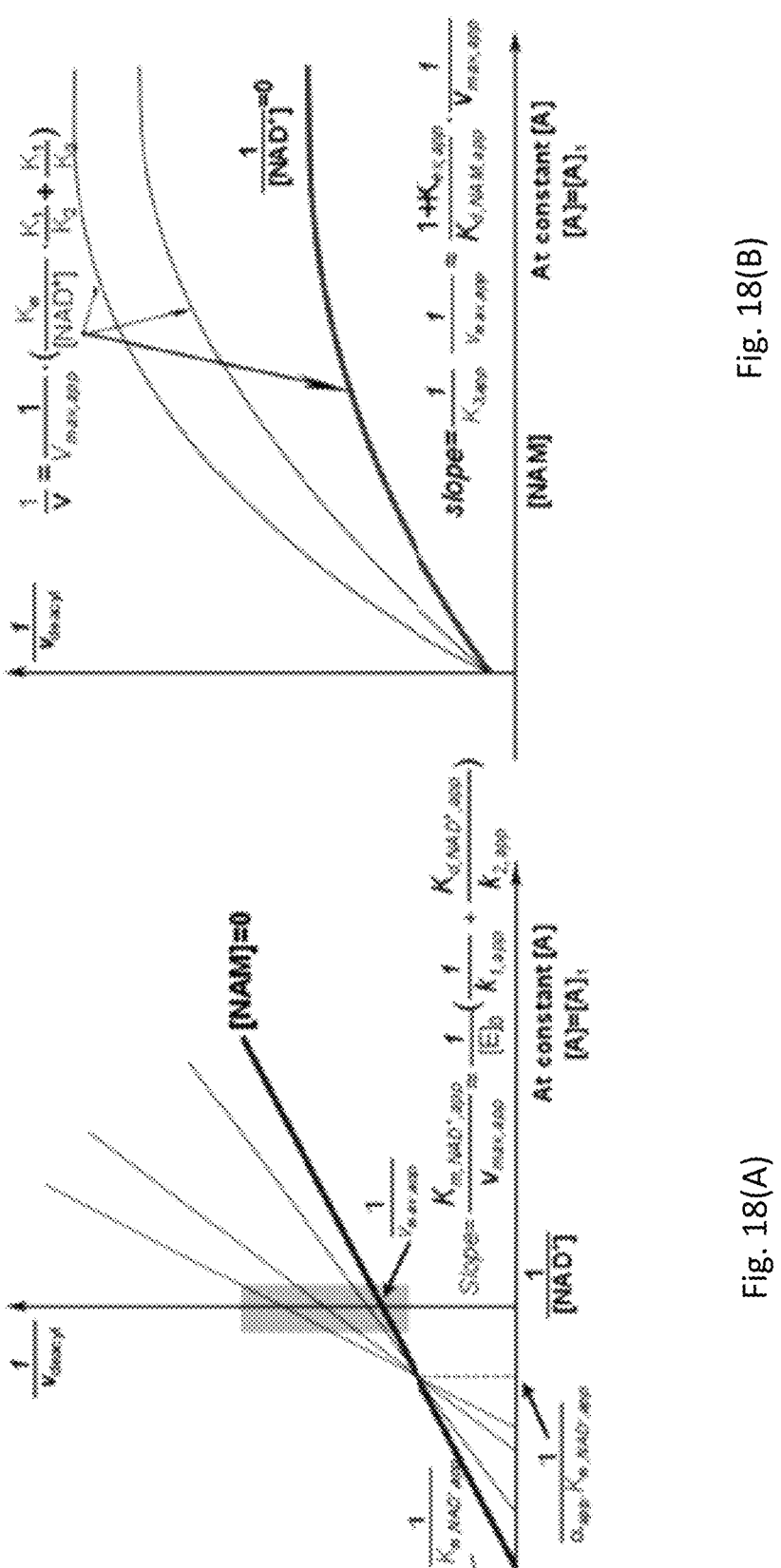
FIGS. 18(A)-18(D)—Mechanism-based activation of sirtuin enzymes: model-predicted steady-state and dose-response properties.
Figures 18C, 18D:
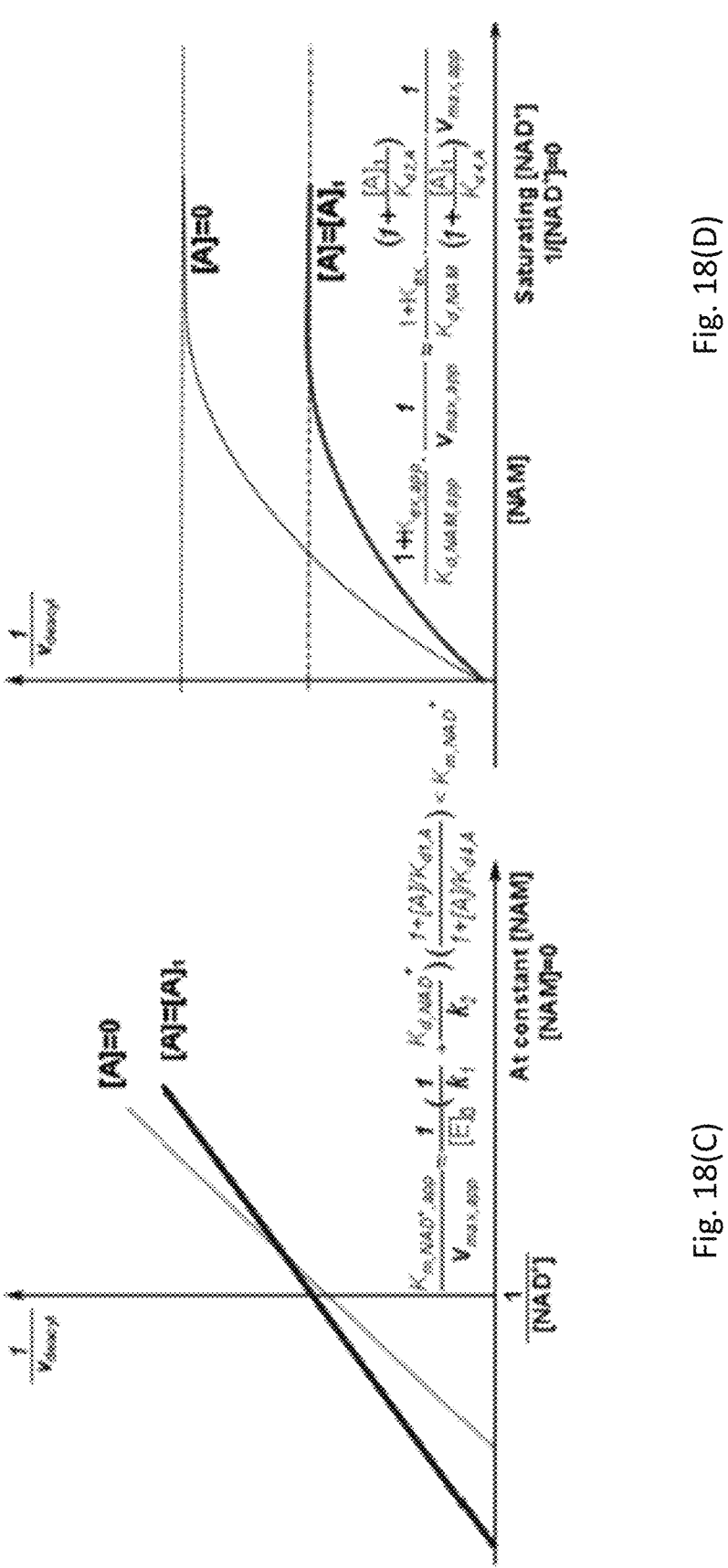
Figures 19A, 19B, 19C:
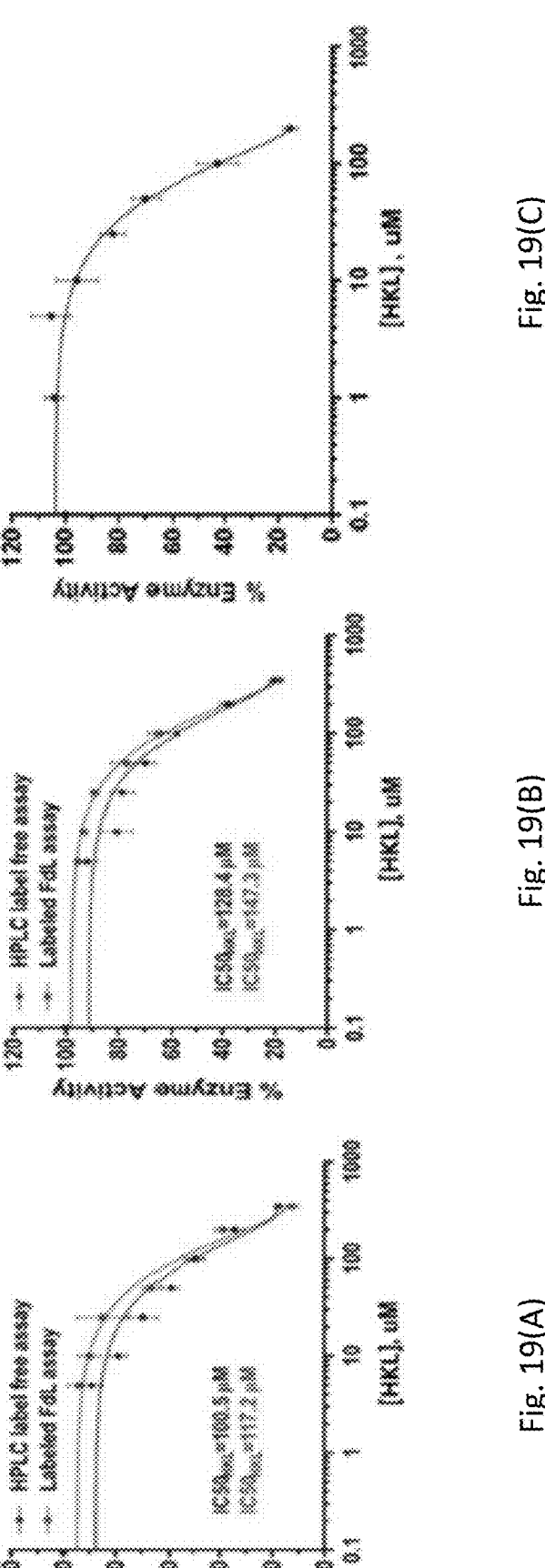
FIGS. 19(A)-19(C)—Dose response of HKL for FdL (fluorolabeled p53-AMC)peptide using label-free HPLC assay and labeled FdL assay FIGS. 19(A) and 19(B) and for MnSOD K122 peptide FIG. 19(C). Dose-response curves were measured under conditions where [E]0/[S]0<<1, where [S]0 denotes the initial concentration of the limiting substrate, in order to maximize the contribution the steady state phase of the reaction to the curve.

We now consider the effects of HKL on SIRT3 ligand binding affinities and steady state activity against the MnSOD substrate. According to FIG. 9B, $K_{d,NAD+}$ is roughly unchanged or slightly reduced for this substrate, implying that $K_{d1,A} \approx K_{d2,A}$. In the traditional picture, based on this data HKL binding would be characterized as noncompetitive with respect to $NAD^+$. According to FIG. 9D, the increase in HKL binding affinity in the presence of NAM suggests that $K_{d,NAM}$ decreases for this substrate, implying that $K_{d3,A} > K_{d4,A}$ in FIG. 17. In the traditional picture of enzyme activity modulation, HKL binding is uncompetitive with respect to NAM.

However, the effect of HKL on activity can only be understood by application of the full kinetic and thermodynamic model described above, which involves simultaneous effects of the modulator on both the forward and reverse reactions in the context of a steady-state model of the reaction. Note that in the presence of HKL, $K_{m,NAD+}$ increases and steady state catalytic efficiency decreases by a somewhat larger margin. The parameter estimates in Table 1 together with the full set of MST binding affinity data can be interpreted within the context of the model above to shed light on the mechanism of HKL modulation and to evaluate its properties as a hit compound.

The aim of steady state characterization of hit compounds for mechanism-based activation is to estimate the parameters in Eq. (1) in the absence of modulator and at a saturating concentration of modulator, varying both $[NAD^+]$ and [NAM] in each case. This provides estimates of both the front and back face steady state parameters in the model. By contrast, a mixed inhibition model with respect to the modulator concentration (as, e.g., applied to certain mechanism-based inhibitors would not have an interpretation for the steady state constants in terms of fundamental rate constants in the sirtuin mechanism, whereas characterizing unsaturating modulator concentrations at each of multiple product (NAM) concentrations, while providing more information, would similarly estimate only apparent steady state parameters.

First, note from Table 1 that $K_1$ decreases several fold in the presence of HKL, consistent with the increase in NAM binding affinity suggested by MST measurements. A decrease in $K_1$ may be inconsequential in terms of a molecule's propensity to increase the enzyme's catalytic efficiency as long as the common assumption of fast NAM release (fast $k_{-3}$ approximation) holds.

Second, $K_3$ decreases several fold in the presence of HKL (Table 1), whereas an increase in $K_3$ is desirable. However, $K_1/K_3$ remains roughly unchanged, as can be observed graphically in FIGS. 8B, D where the effect of $K_1$ becomes diminished at high [NAM]. This indicates that the reduction in $K_{d,NAM}$ may be playing an important role in the observed reduction of $K_3$. Under the approximations, the modulated $K_{ex}'$ may be relatively close to $K_{ex}$. This is a favorable property of a hit compound since it would imply $K_{d3,A} \approx K_{d2,A}$; hit evolution could be carried out to reduce $K_{d3,A}$, which is conducive to activation. Note that since $K_{d,NAD+}$ remains roughly unchanged by the modulator, if $K_{ex}$ is also roughly unchanged, any reduction in $k_2$ that affects $K_m$ (see Eq. (2)) is associated with a similar reduction in $k_{-2}$.

Third, $\alpha$ decreases several fold in the presence of HKL (Table 1 and expression (3) for a). This shifts the intersection point of the lines in FIG. 7A to the left in FIG. 7B (see FIGS. 18(A)-18(D) for a graphical depiction of $\alpha^* K_{m,NAD+}$ in terms of the intersection point). Under the above hypotheses that $K_{d2,A} \approx K_{d1,A}$, $K_{d3,A} \approx K_{d2,A}$, and $K_{d3,A} > K_{d4,A}$, this is expected according to the expressions for $K_{2,app}$ and $K_{3,app}$ in FIG. 16. This decrease in a is due to the fact that $K_m$ increases in the presence of HKL while $K_{d,NAD+}$ does not increase/decreases slightly (see Eq. (3)). MST results on HKL's effect on $K_{d,NAD+}$ (FIG. 9B) are consistent with the reduction in $a^* K_{m,NAD+}$ obtained from the steady state parameters in Table 1. According to Eq. (3), $\alpha^* K_{m,NAD+}$ is highly correlated with $K_{d,NAD+}$ and the methods are complementary, since MST employs a chemically modified $NAD^+$ analog. Moreover, a slight decrease in $K_{d,NAD+}$ but increase in $K_{m,NAD+}$ can explain the observed non-steady state activation in the case of this substrate (see below). We can also observe by comparing FIGS. 8 C, D to A, B that in the presence of NAM, the extent of steady state inhibition by HKL diminishes, and that due to the reduction in a, this effect is most pronounced at low $[NAD^+]$, which is the condition under which activation is therapeutically most useful. Under the above hypotheses, through further hit to lead evolution, this property might be exploited to activate the enzyme under steady state conditions at low $[NAD^+]$ in the presence of physiological [NAM] or, going further, to allow a $K_m$ decrease in the absence of product.

Finally, the observed increase in HKL binding affinity in the presence of O-acetylated ADP ribose coproduct (FIG. 10A) may be consistent with the decrease in $k_{cat}$ if product release is rate limiting for this substrate. Also, stabilization of coproduct binding may be consistent with HKL favoring a closed over an open loop conformation; for example, Ex-527, which is known to preferentially bind to a closed loop conformation, reduces coproduct dissociation rate and improves its binding affinity.

We can also understand the properties of conventional steady state inhibition plots with respect to modulator concentration based on the mechanistic information gleaned from our studies. Note from FIG. 8A, the intersection point of the lines with and without modulator lies to the left of the y axis and above the x axis. In the traditional mixed inhibition picture of steady state enzyme modulation (which does not distinguish between $K_m$ and $K_d$), this is due to the modulator both increasing $K_m$ and decreasing $v_{max}$, but this traditional picture does not distinguish between $K_m$ and $K_d$, and also does not account for the relation between $K_m$ and $v_{max}$. By contrast, the equations for the lines in the presence and absence of modulator can be understood in terms of the fundamental dissociation constants and rate constants of the reaction based on our mechanistic analysis above.

Figures 8C, 8D:
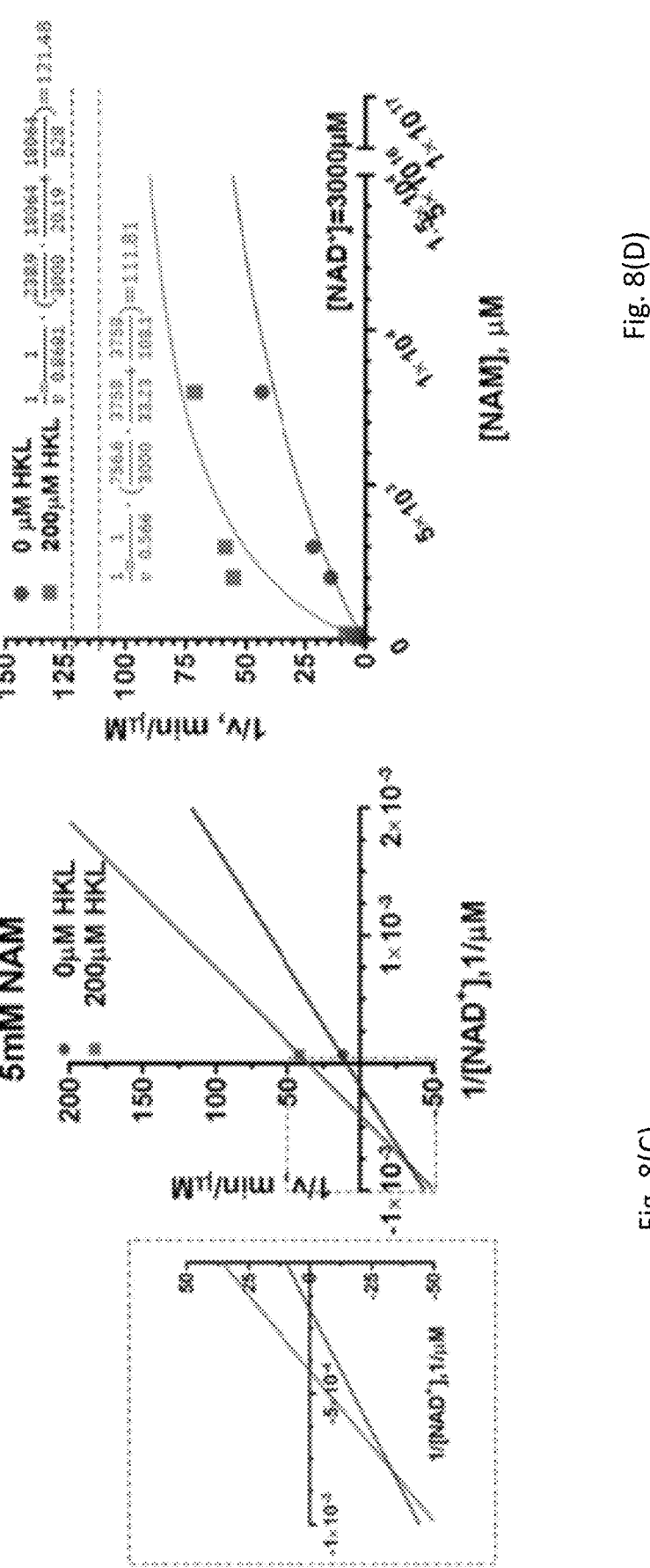

Note also from FIG. 8C, the intersection point of the lines with and without modulator moves closer to the x axis in the presence of NAM. For sufficiently high [NAM], the intersection point of these lines falls below the x axis and then will eventually move to the right of the y axis. The fact that HKL does not increase $K_{d,NAD+}$ gives it higher relative activity at low [NAD$^+$] in presence of NAM (this is especially pronounced in the pre-steady state phase, see inset in FIG. 7D and also FIGS. 12,13). If this could be achieved in the absence of NAM, it would signify an activator that increases steady state catalytic efficiency while reducing $v_{max}$.

The ability to relate the modulated steady state kinetics of the enzyme to the manner in which a hit compound interacts with the various species in the reaction mechanism is a feature of mechanism-based activator discovery, in contrast to hit validation in traditional drug discovery, where the focus is on binding affinities.

Figures 13A, 13B:
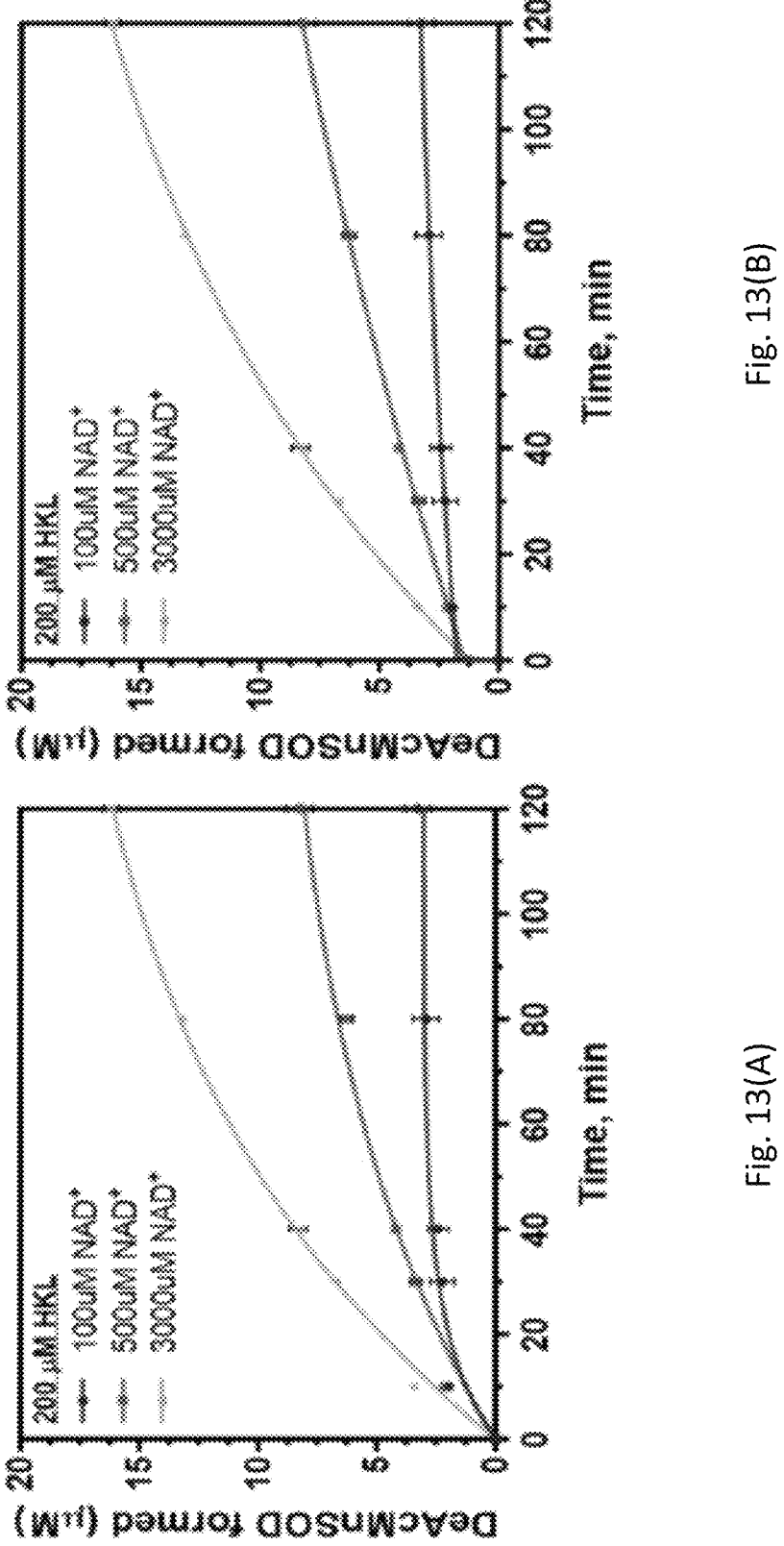
FIGS. 13(A)-13(C)—Sirt3 deacetylation activity in the presence of Honokiol for different cofactor ($NAD^+$) concentrations: steady state rate determination. Plots of DeAc-MnSOD formed vs. time with FIG. 13(A) single exponential fitting, and FIG. 13(B) double exponential fitting. Corresponding linear rate fitting plots for FIG. 13(C) double exponential (steady state rates) starting at 10 min. [NAM]=100 µM.
Figure 13C:
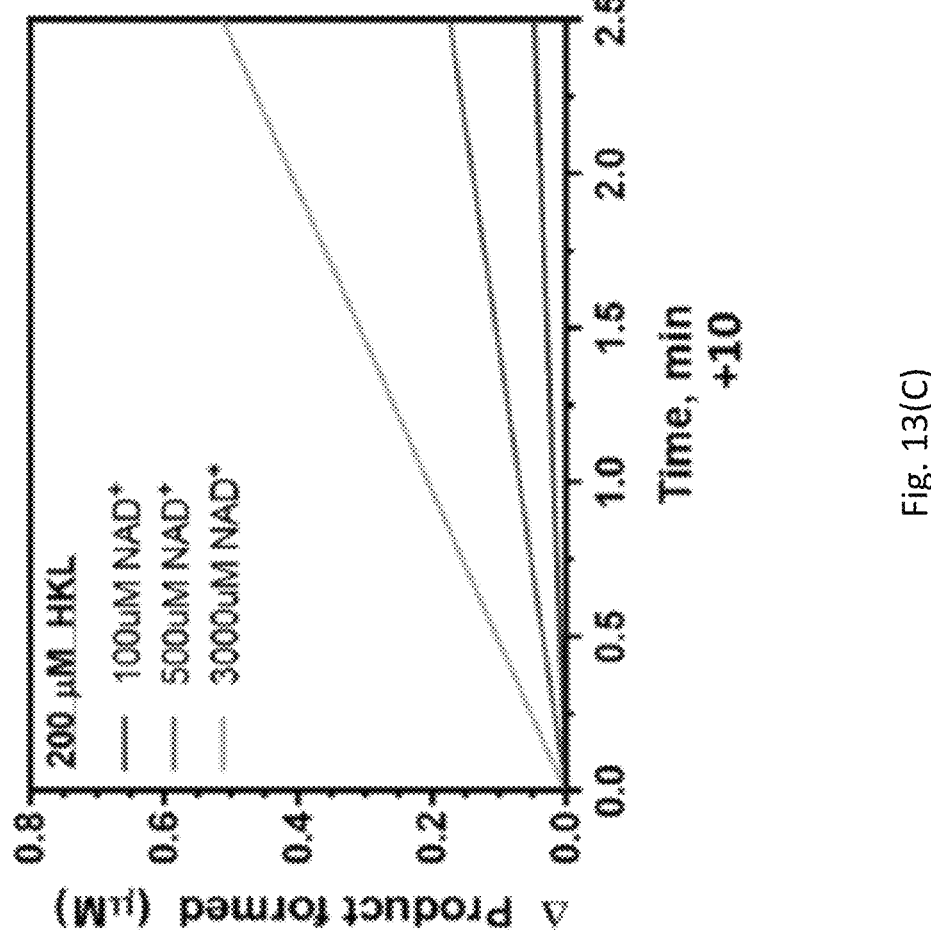

Pre-steady state kinetics can provide additional information about the mechanism of modulation, as discussed further below. For enzymes where product dissociation is the rate-limiting step, initial rates may not be similar to steady state rates. Hence, using initial rates in inhibition model fittings can be used for qualitative model selection, not quantitative parameter estimation. In the present work, we applied double exponential time series fits for quantitative work, which accounted for the possibility of a pre-steady state phase affecting initial rates (FIG. 13). Had we fit a single exponential, the estimated $v_{max}$s would be similar but the estimated Kms would decrease, increasing the estimated catalytic efficiency in in the presence of HKL beyond what we have reported. Importantly, if slow product dissociation results in the significantly slower turnover rate in the steady state phase, then HKL may not reduce the rate of the slowest deacylation chemistry step in stage 2 of the reaction (discussed further below).

Turning to the p53-AMC substrate, which compares the initial rates of catalysis with this substrate in the presence and absence of saturating HKL, we observe a change in $v_{max}$ but not $K_m$—which would be characterized as noncompetitive inhibition in the traditional picture. However, as discussed above for the MnSOD substrate, the traditional picture is not sufficiently informative and the mixed inhibition plots with respect to NAM provide the important mechanistic information. In the absence of NAM, there is a 3-4 fold decrease in steady state catalytic efficiency for this substrate. However, whereas a decreased in the presence of HKL for the MnSOD substrate, it increases for the p53-AMC substrate. Since for MnSOD substrate, there was no increase in $K_{d,NAD+}$ and a reduction in $\alpha^*K_{m,NAD+}$ induced by HKL, the increase in $\alpha^*K_{m,NAD+}$ induced by HKL for p53-AMC substrate is consistent with the increase in $K_{d,NAD+}$ as measured by MST (FIG. 11). Taken together with the significant pre-steady state activation induced by HKL for this substrate (FIG. 6C), this also demonstrates that reduction in $K_{d,NAD+}$ is not the only means for activation by HKL, consistent with the theory of mechanism-based activation.

Having identified a hit compound for mechanism-based activation, we can now use the kinetic and thermodynamic data above—which together constitute a complete set of measurements—to simultaneously estimate all the modulated rate constants $k_1'$, $k_{-1}'$, $k_2'$, $k_{-2}'$, $k_3'$, $k_{-3}'$, $k_4'$ and—associated free energy changes in the presence of the modulator. The ability to identify system parameters in this manner will allow rapid characterization of mutated hit compounds during hit-to-lead evolution to identify those with a favorable balance of properties suitable for further development.

The mechanistic analysis presented herein is necessary to understand effects of hit compounds like HKL on sirtuin activity because the net effect of activation or inhibition depends on precise physiological conditions. The current theory explains this dependence. The dependence on time of the relative rates of MnSOD peptide deacylation with and without HKL (FIG. 12) is relevant to the physiological effects of HKL on SIRT3 deacylation in vivo. HKL increases the rate at short times, pointing to the importance of non-steady state effects In particular, the ratio $[E]_0/[S]_0$, where $[S]_0$ denotes the initial concentration of the limiting substrate, plays a critical role in determining the relative contributions of non-steady state activating phases and steady state inhibitory phases to the net enzyme activity—with higher values of this ratio increasing the extent of activation. It was observed that SIRT3 expression levels increase in the presence of HKL, which is consistent with our mechanistic analysis as it will offset the effect of product inhibition especially in the limit of low [NAD$^+$]. Finally, it is also possible to carry out analogous characterization experiments at unsaturating HKL in the dose response curves (at $[E]_0/[S]_0 \ll 1$), in order to obtain the apparent steady state constants defined in FIG. 16. The use of unsaturating modulator concentrations can allow the modulator to dissociate from the product complex, thus enabling product release. Note that the first-order rapid equilibrium segments approximations above to the steady state constants in the presence of modulator (FIG. 16) do allow for the possibility of an activity maximum at subsaturating concentrations. These points are all explored in further detail in the sections below.

In summary, HKL binds to all complexes in the sirtuin reaction mechanism, not just the product as in the case of mechanism-based sirtuin inhibitors like Ex-527. The tight binding of HKL to the coproduct does not reduce catalytic efficiency. Compounds like Ex-527 do not bind to any other catalytically relevant complexes and because they reduce product dissociation rate significantly, thus extinguishing the reaction under saturating conditions. Comparing the effects of saturating HKL and saturating Ex-527 on SIRT3 activity, due to the substantial reduction in coproduct dissociation rate (steady state $k_{cat}$ close to 0), saturating Ex-527 effectively constitutes "single hit" conditions wherein each enzyme can only turn over products once. Ex-527 does this for many substrates and sirtuins including AceCS2 and p53-AMC, due to the fact that it protrudes into the C pocket and is hence incapable of binding $NAD^+$ in a productive conformation. HKL is a hit for both MnSOD and p53-AMC substrates for reasons discussed above.

X. Apparent Steady State Effects of Unsaturating Concentrations of MB-STAC Hit Compounds Although saturating [A] is needed to characterize the effects of a MB-STAC hit compound on the chemical and binding rate constants of the reaction, the hit compound can be applied at unsaturating concentration in order to leverage the positive effects of A on certain steps of the reaction while reducing its negative effects on other steps. At unsaturating [A], the reaction can follow a path between the front and back faces of the cube resulting in apparent steady state constants.

As such, note that the physiological effect of HKL activation was reported at 10 µM concentration, and this is the concentration at which we reported non-steady state activation in FIGS. 6B,C. At this concentration, there is very little net effect of HKL on activity in the steady state dose-response curves of FIG. 6A. Note that 10 µM HKL is above the $K_d$ of the compound as displayed in FIG. 9 (also note there is no secondary binding event at higher [HKL] as shown in this graph). However, the effect of HKL on activity in the steady state dose response curve in FIG. 6A extends above 100 µM HKL. This is because the relative rates of association/dissociation of HKL to/from the enzyme compared to the other rate constants of the reaction can affect the apparent values of the steady state rate constants and this effect is essentially eliminated at HKL concentrations above 100 µM. On the other hand, unsaturating HKL can allow the apparent steady state and rate constants for steps such as coproduct release to be increased with respect to the values of these constants in the presence of HKL. Nonetheless, hit-to-lead evolution and lead optimization of MB-STACs should be carried out at saturating [A] (as applied above) in order to increase the robustness of the MB-STAC with respect to physiological expression level and substrate level differences. It is emphasized that the experimental dose response curves above were intentionally collected at saturating HKL since these properties are most relevant to hit-to-lead evolution.

IX. Non-Steady State Activation by MB-STAC Hit Compounds

The steady state dose response curves displayed in FIG. 6A were intentionally measured at low $[E]_0/[NAD^+]_0$ and at saturating HKL for the purpose of characterization of the effects of HKL on deacetylation reaction parameters. Overall, the reaction goes through 3 phases: i) the first (pre-steady state) phase during which each enzyme molecule catalyzes a limited number of reaction cycles, and which is faster in the presence of saturating HKL (FIG. 12); ii) the second (steady-state) phase during which each enzyme molecule may catalyze many reaction cycles, and which is slower in the presence of saturating HKL; iii) the third (post-steady state) phase which is faster in the presence of saturating HKL, once the concentration of the limiting substrate is similar to or lower than the concentration of enzyme. Depending on the initial ratio of enzyme to limiting substrate in the system (and the ratio of enzyme to HKL concentration, as described in the previous section), the net effect of HKL over the course of the reaction can be either inhibitory or activating, with activation occurring if this ratio is above a threshold value. As the initial ratio of enzyme concentration to limiting substrate concentration increases, the duration of the first two phases decreases and the duration of the third phase increases. If this ratio is not low, steady state rate measurements needed to characterize the effects of HKL are not accurate.

The first two phases have been studied experimentally above. The role of product inhibition in non-steady state activation by HKL is apparent from FIG. 12A,C. It can be seen that activation occurs at times prior to which the amount of product formed is roughly equal to the enzyme concentration $[E]_0$. FIGS. 6B and C, which show activation with high statistical significance, use measurements from reaction phase i. The dose response curve for 100 uM NAD+, 100 uM NAM (FIG. 6A) includes contributions from phases i and ii of the reaction, whereas the other dose response curves have dominant contributions from phase ii (steady state phase).

The pre-steady state activation presented in FIG. 12 for the MnSOD substrate (for both saturating and unsaturating HKL) implies that the third phase will also display activation for this substrate.

The results from numerical simulation of SIRT3 reaction dynamics for various values of $[E]_0/[NAD^+]_0$ (FIGS. 14, 15) are fully consistent with the analysis above of the effects of HKL on the three phases of the reaction, and the pre-steady state activation/steady state inhibition observed experimentally. In FIG. 14 ($[E]_0/[NAD^+]_0 \ll 1$), note the pre-steady state activation by the MB-STAC followed by a long steady state phase and finally a post-steady state phase. In FIG. 15 (higher $[E]_0/[NAD^+]_0$), note the net activation, and also the shorter steady state phases which preclude accurate parameter estimation.

In the presence of HKL, $k_{cat}$ in the steady state model does not correspond to the rate determining step under non-steady state conditions; rather, being the rate limiting step of product release and the final chemistry step, it is approximately equal to the rate of product release. Since the rate determining step under non-steady state conditions is the final (deacetylation) chemistry step, the pre-steady state activation (FIG. 12) of SIRT3 by saturating HKL, as reported above, indicates that HKL reduces the rate of product release, but not necessarily the rate of the final chemistry step. Non-steady state (phases i and iii defined above) measurements do not provide information on the effect of a modulator on product release, while measurements on the steady state system do not distinguish between effects the modulator has on the rate of product release and the rate of the final chemistry step. Thus the two types of measurements play complementary roles in the characterization of hit compounds for mechanism-based activation.

Importantly, note that in the expression for the steady state catalytic efficiency $k_{cat}/K_{m,NAD+}$, which is relevant to steady state sirtuin activation under $NAD^+$ depletion conditions associated with aging, the rate constants in $k_{cat}$ do not explicitly appear. Thus the reduction in $k_{cat}$ by such a modulator does not affect catalytic efficiency. Hence the non-steady state activation by HKL is relevant to the goal of increasing catalytic efficiency, but further hit-to-lead evolution is required.

Note that in order to characterize the mode of action of the mechanism-based inhibitor Ex-527, standard inhibition models were not sufficient, requiring reference to crystal structures. We have presented quantitative methods for the characterization of mechanism-based activator hits that are suitable for higher throughput studies. These data can be applied to the system identification of the effects of HKL on all rate parameters, through a combination of the steady state/thermodynamic analysis reported above and time series analysis on the non-steady state kinetic data, as described in reference.

We have applied a biophysical framework for activation of sirtuin enzymes to the characterization of proposed non-allosteric sirtuin activators of the SIRT3 enzyme. We presented and analyzed results from computational, kinetic and thermodynamic studies on these modulators. Two different peptide substrates were studied to show how the substrate dependence of mechanism-based activation can be explored using the present framework.

We have shown that the compound honokiol, previously reported to be a SIRT3 activator, does activate the enzyme under physiologically relevant non-steady state conditions but does not activate it under steady state conditions. By applying a) computational modeling; b) experimental non-steady state, steady state and thermodynamic assays, and using the theory of mechanism-based enzyme activation to interpret the data, we explained the mechanism behind honokiol's enhancement of SIRT3's non-steady state deacetylation rate, demonstrated it is a nonallosteric modulator, and established a foundation for further hit-to-lead evolution of honokiol and related compounds in order to convert them into more potent, steady state activators. As such, the present study constitutes an important foundation for the development of a new class of drugs for the treatment of age-related diseases that operate through a wholly new mode of action not shared by any existing drug.

The enzyme activation theory that was applied herein these modulators motivates computational and experimental workflows for the hit identification, hit-to-lead evolution, and lead optimization of mechanism-based activators. In particular, the theory enables the identification of important hits that activate enzymes in a dose-dependent fashion or under non-steady state conditions, and evolution of these hits into more robust steady state activators. This is achieved through separation of the observed kinetic and thermodynamic effects of a modulator into components and identification of those properties that require optimization through hit-to-lead evolution. Hit-to-lead evolution could be applied, for example, to HKL modulation of the deacylation rate of specified SIRT3 substrates. Such workflows would bear more similarity to enzyme directed evolution than to traditional drug discovery workflows. Additional work can apply enzyme engineering-inspired methods to hit-to-lead evolution of nonallosteric activators, in conjunction with structure-based computational methods analogous to those developed for computational enzyme design.

Materials and Methods

Chemicals and Reagents

MnSOD (KGELLEAI-(KAc)-RDFGSFDKF), SEQ ID NO: 1, was synthesized by GenScript (Piscataway, NJ). FdL2 (QPKK$^{AC}$-AMC) peptide, also called p53-AMC peptide, SEQ ID NO: 2, was purchased from Enzo Life Sciences (Farmingdale, NY).

Expression and Purification of hSirt3$^{102-399}$ hSirt3$^{102-399}$ was expressed in *E. coli* Arctic Express (DE3) cells (Agilent Technologies, Wilmington, DE). A single bacterial colony was inoculated in LB media containing ampicillin and gentamycin at 37° C. For protein purification, we inoculated overnight grown culture into 200 ml LB medium and grown at 30° C., 250 rpm for 4 hours. We induced Sirt3 expression by adding 1 mM IPTG at 15° C. After 24 hours, cells were harvested, and the pellet was re-suspended in A1 buffer (50 mM NaH$_2$PO$_4$, 300 mM NaCl, 10 mM imidazole, pH 8.0) and sonicated. A clear supernatant was obtained by centrifugation at 14000×g for 25 min at 4° C. then loaded onto a 5 ml HisTrap HP column, pre-equilibrated with A1 buffer, attached to an AKTA pure FPLC system (GE Healthcare, Pittsburgh, PA). The column was then washed with 50 ml each buffer A1, A2 (50 mM NaH$_2$PO$_4$, 300 mM NaCl, 75 mM imidazole, pH 8.0), A3 (20 mM Tris-HCl, 2M urea, pH 6.8), and again with buffer A2. Protein was eluted with buffer B1 (50 mM NaH$_2$PO$_4$, 300 mM NaCl, 300 mM imidazole, pH 8.0). The protein fractions were pooled, dialyzed against dialysis buffer (25 mM Tris, 100 mM NaCl, 5 mM DTT, 10% glycerol, pH 7.5) at 4° C. overnight. The purity of final protein was >85% as assessed by SDS-PAGE.

Effect of Honokiol on hSirt3$^{102-399}$ deacetylation activity for MnSOD and FdL2 peptides Steady state enzymatic reactions used 2.5 mM NAD$^+$ and 6.25 µM MnSOD peptide or 50 µM NAD$^+$ and 600 µM peptide substrate, in the presence and absence of HKL (0-200 µM), in the following buffer: 50 mM TRIS-HCl, 137 mM NaCl, 2.7 mM KCl, and 1 mM MgCl$_2$, pH 8.0 and 5% DMSO. Reactions were started by adding 5U (2.17 µM) hSirt3$^{102-399}$ and then incubated at 37° C. for 30 minutes. Reactions were terminated using TFA. For reactions with FdL2 peptide, we terminated the reactions at specified times using 1× developer and measured fluorescence on TECAN microplate reader. The raw data were fitted to the specified model equations with GraphPad Prism (GraphPad Software, Inc, CA).

Separation of MnSOD Peptide

An Agilent 1260 infinity HPLC system and a ZORBAX C18 (4.6×250 mm) column were used to separate deacetylated peptide and acetylated substrate using gradient comprising 10% acetonitrile in water with 0.005% TFA (solvent A) and acetonitrile containing 0.02% TFA (solvent B) 1 ml/min flow rate.

Solubility Measurements

Solubilities of Honokiol, DHP-1, and DHP-2 were measured using HPLC (Agilent 1100 series). Samples were prepared by adding known amounts of the compounds in HDAC buffer containing a range of DMSO concentrations. The samples were allowed to equilibrate at 25° C. for 48 hours before analyzing on calibrated HPLC; over-saturated samples were prepared by adding excess compound into the solvent mixtures of interest. The linearity was measured by R-values at least >0.99 and the estimated detection limit was around 0.002 mg/mL (2 g/mL) based on an acceptable S/N ratio.

hSirt3$^{102-399}$—Ligand Binding Assay by Microscale Thermophoresis

DY-647P1-NHS-Ester conjugated hSirt3$^{102-399}$ was used for MST studies. Briefly, the protein conjugation was done in 1×PBS pH 7.4, 0.05% Pluronic F-127, and the labeled protein was buffer exchanged into 47 mM Tris-HCl pH 8.0, 129 mM NaCl, 2.5 mM KCl, 0.94 mM MgCl$_2$, 5% DMSO, 0.05% Tween-20. We used 2 nM labeled hSirt3 and titrated with varying concentrations of the modulators in the absence and presence of various concentrations of substrates, products and intermediates. The thermophoresis was measured (excitation/emission 653/672 nm) using a Monolith NT. 115 Pico (NanoTemper Technologies) at 25° C. Dissociation constants (K$_d$) were determined using GraFit7 (Erithacus Software) by nonlinear fitting.

Preparation of SIRT3.Ac-Pr.NAD$^+$ Substrate Complex for Protein-Ligand Docking

Modeling the SIRT3 complex structure. The SIRT3 receptor structure for docking was prepared by converting Carba-NAD in pdb structure 4FVT into NAD$^+$. An additional receptor structure for docking was prepared by replacing the cofactor binding loop in 4FVT with that from 4BVG. The complex structures were subjected to the Protein Preparation Wizard module of Schrodinger Suite. The module assigns bond orders and adds hydrogens based on Epik calculations for proper pKa values. Het molecules except for native ligands were eliminated and optimized of their complex structure by the Prime module of Schrodinger suite. The side chain structure of HIS248 was modified to HIE, because N of the proximity of the histidine to the ribose oxygen of NAD.

MD simulation protocol. The SIRT3-ALY-NAD$^+$ complex was subjected to molecular dynamics simulation as follows. Initially, the complex is kept into a suitably sized box, of which the minimal distance from the protein to the box wall was set to 10 A. The box is solvated with the SPC (simple point charge) water model. The counterions are added to the system to provide a neutral simulation system. The whole system was subsequently minimized by using OPLS2005 Force field. The charges of the atoms of NAD$^+$ and ALY were calculated by using OPLS2005 Force field. Covalent and non-bonded parameters for the ligands atoms were assigned, by analogy or through interpolation, from those already present in the OPLS2005 force field. MD simulation is then carried out using the Desmond package (version 2.3) with constant temperature and pressure (NPT) and periodic boundary conditions. The OPLS2005 force field was applied for the proteins.

The default Desmond minimization and equilibration procedure was followed. Simulations were kept at constant pressure (1 bar) and temperature (300 K) maintained with a Berendsen barostat and thermostat, respectively. SHAKE was applied to all systems allowing a 2-fs time-step. Long-range interactions were treated with the Particle Mesh Ewald method for periodic boundaries using a nonbonded cut-off of 9.0 and the nonbonded list was updated frequently using the default settings. Coordinates and energies for the OPLS2005 force field simulations were recorded for total of 15 ns. The structure of the equilibrium state (15 ns) was extracted from the MD. Het molecules except for native ligands were eliminated (water and counter ions for MD). Minimization was performed using the OPLS3e force field to produce the MM-optimized reactant structure.

OM-AMI optimization of the SIRT3 complex. The minimized SIRT3-ALY-NAD$^+$ complex structure optimized using the OPLS2005 force field was further optimized at the QM/MM (DFT-B3LYP/6-31G*: OPLS2005) level, using the Qsite module as implemented in Schrodinger Suite. The quantum mechanics (QM) region of reactant includes the NAD$^+$, acetyl lysine entire residue of peptide, GLN 228 entire residue of receptor and side chain (CH2C3N2H3) of HIS248, for a total of 132 atoms. The QM region was calculated by using the density functional theory with the B3LYP exchange-correlation functional and 6-31G* basis set. The remainder of the system (MM region) was treated by using the OPLS2005 force field. A total of 4023 atoms in the system were included in QM/MM simulations. To avoid over polarization of QM atoms by MM atoms at the boundary, Gaussian charge distributions were used to represent the potential of the atoms within two covalent bonds of the QM/MM cut-site using the Gaussian grid method for hydrogen cap electrostatics in QSite. MM point charges were employed for the rest of the MM region.

Protein-Ligand Docking

Molecular dockings of compounds to SIRT3 ligand complexes were carried out by AutoDockVina as previously described [28]. AutoDockTools was used to prepare the receptor PBQT format adding polar hydrogen and assigning Gasteiger charges to all its atoms as well as identifying the coordinates of the target box to enclose QM/MM optimized SIRT3.Ac-Pr.NADY substrate for global docking with a cubic grid box of 126×126×126 point dimensions of 0.5 resolution. Prior to docking, compounds were geometry optimized in gas phase by Hartree-Fock method with 6-311G+ basis.

Loop Modeling and Binding Affinity Calculations

The following protocol was used to prepare starting structures for molecular dynamics simulation of the SIRT3 ternary (SIRT3+AcPr+NAD$^+$), intermediate (SIRT3+ADPR-Pr-Im) and product (SIRT3+Pr+AADPR) complexes with native and nonnative loop for conformational statistics and binding affinity calculations, as previously described. For simulations with nonnative loops, in the case of the ternary complex (prepared based on the 4FVT crystal structure for all protein residues except the cofactor binding loop), the intermediate (closed) conformation of the cofactor binding loop (residues 155-178) was substituted; whereas in the case of the coproduct complex (prepared based on 4BVH crystal structure), the apo (open) conformation of the cofactor binding loop (residues 155-178 from the 3GLS crystal structure) was substituted.

Binding affinities and conformational energies were calculated by the MD/MM-GB(PB)SA method.

---

The invention claimed is:

1. A method for identifying a test compound for a mechanism-based sirtuin activating compound (MB-STAC), the method comprising:

establishing a library of compounds on the basis of the compounds exhibiting computational docking with at least one sirtuin complex selected from the group consisting of sirtuin+peptide substrate complex, sirtuin+peptide substrate+NAD$^+$ complex, sirtuin+alkylimidate intermediate+NAM complex, sirtuin+alkylimidate complex, and sirtuin+O-AADPR complex; and a) incubating a test compound from the library of compounds with a sirtuin enzyme (E), NAD$^+$, NAM, and a concentration of an acylated substrate peptide in an assay for deacylation activity;

b) measuring non-steady state ($v_{non-ss}$) rate of sirtuin enzyme-catalyzed deacylation; and c) identifying the test compound as a hit compound when the test compound induces sirtuin enzyme activation at an $[E]_0/[NAD^+]_0$ ratio greater than 0.25 and less than 1.

2. The method of claim 1, wherein an $[E]_0/[test compound]_0$ ratio is at least 0.088.

3. The method of claim 1, wherein the non-steady state ($v_{non-ss}$) rate of sirtuin enzyme-catalyzed deacylation is measured when the enzyme concentration exceeds deacylated product concentration.

4. The method of claim 1, wherein a value of less than 1 of the $[E]_0/[NAD^+]_0$ ratio permits measurement of enzyme activity when the enzyme concentration exceeds deacylated product concentration.

5. The method of claim 1, wherein the test compound interacts with the sirtuin enzyme cofactor binding loop.

6. The method of claim 5, wherein the test compound forms hydrogen bonding interactions with one or more amino acid residues of the sirtuin enzyme cofactor binding loop.

7. The method of claim 6, wherein the test compound interacts with one or more of Glu 177, Asp 156, and Phe 157 of the cofactor binding loop of a SIRT3 enzyme, or homologous residues in other sirtuin enzymes.

8. The method of claim 5, wherein the test compound forms non-polar interactions with one or more amino acid residues of the cofactor binding loop.

9. The method of claim 5, wherein the test compound induces one or more conformational changes in the cofactor binding loop.

10. The method of claim 1, wherein the test compound interacts with a binding pocket of the sirtuin enzyme.

11. The method of claim 1, wherein a compound of the library is identified as test compound if the compound:

a) exhibits computational docking with at least one of the sirtuin+peptide substrate+NAD+ complex and sirtuin+alkylimidate intermediate+NAM complex; and b) ratios of dissociation constants for binding of the compound to the sirtuin+peptide substrate complex, sirtuin+peptide substrate+NAD+ complex, sirtuin+alkylimidate intermediate+NAM complex, and sirtuin+alkylimidate complex, denoted by $K_{d1,A}$; $K_{d2,A}$; $K_{d3,A}$; and $K_{d4,A}$ respectively, satisfy at least one of the following relations:

$$\frac{K_{d1,A}}{K_{d2,A}} \leq 1 \Leftrightarrow \frac{K'_{d,NAD+}}{K_{d,NAD+}} \geq 1$$

$$\frac{K_{d2,A}}{K_{d3,A}} \gg 1 \Leftrightarrow \frac{K'_{ex}}{K_{ex}} \ll 1$$

$$\frac{K_{d3,A}}{K_{d4,A}} \geq 1 \Leftrightarrow \frac{K'_{d,NAM}}{K_{d,NAM}} \geq 1$$

wherein ⇔ means equivalent to, wherein $K_{d,NAD+}$ is the dissociation constant for NAD$^+$, $K_{d,NAM}$ is the dissociation constant for NAM, and $K_{ex}$ is the exchange equilibrium constant, wherein the ' sign denotes corresponding values in presence of the test compound, and wherein $K_{d1,A}$, $K_{d2,A}$, $K_{d3,A}$, and $K_{d4,A}$ are estimated via the computational docking.

12. The method of claim 11, wherein the dissociation constants are determined via combination of molecular mechanics energies with Poisson-Boltzmann or generalized Born and surface area continuum salvation methods.

13. The method of claim 1 further comprising assaying effects of the test compound on sirtuin non-steady state, steady state and equilibrium parameters, the method comprising:

d) fitting the following nonlinear model to steady state rate data:

$$\frac{v}{v_{max}} = \frac{[NAD^+]\left(1 + \frac{[NAM]}{K_1}\right)}{K_{m,NAD^+}\left(1 + \frac{[NAM]}{K_2}\right) + [NAD^+]\left(1 + \frac{[NAM]}{K_3}\right)}$$

wherein v denotes initial deacylation rate;

e) obtaining estimates of steady state parameters $V_{max}$, $K_{m,NAD+}$, $K_1$, $K_2$, $K_3$ in the absence of the test compound and $V_{max,app}$, $K_{m,NAD+,app}$, $K_{1,app}$, $K_{2,app}$, $K_{3,app}$ in the presence of the test compound at a nonzero concentration,
wherein $$\alpha = \frac{K_3}{K_2} \approx \frac{K_{d,NAD+}}{K_{m,NAD+}};$$

$K_{d,NAD+} \approx \alpha * K_{m,NAD+}$, and
wherein the test compound is a hit compound if $K_{d,NAD+}$ in the presence of the test compound is less than $K_{d,NAD+}$ in the absence of the test compound.

14. The method of claim 1 further comprising measuring steady state (v) rate of sirtuin enzyme-catalyzed deacylation at several $NAD^+$ concentrations for each of several NAM concentrations.

15. The method of claim 14, wherein the test compound is a hit compound when the test compound further induces sirtuin inhibition in the steady state.

16. The method of claim 14, wherein a ratio of non-steady state sirtuin enzyme-catalyzed deacylation to steady state sirtuin enzyme-catalyzed deacylation is greater than 1.

17. The method of claim 15, wherein transition from the non-steady state to the steady state occurs after the concentration of the deacylated product exceeds the concentration of the sirtuin enzyme.

18. The method of claim 1, wherein the concentration of an acylated substrate peptide is a saturating concentration.

\* \* \* \* \*